US011266746B2

(12) United States Patent
Oppenheim et al.

(10) Patent No.: US 11,266,746 B2
(45) Date of Patent: Mar. 8, 2022

(54) THERAPEUTIC ANTITUMOR COMBINATION OF A TLR4 LIGAND WITH OTHER TREATMENTS

(71) Applicant: THE UNITED STATES OF AMERICA, as represented by the Secretary, Department of Health and Human Services, Bethesda, MD (US)

(72) Inventors: Joost J. Oppenheim, Rockville, MD (US); De Yang, Frederick, MD (US); Zhen Han, Frederick, MD (US); Joseph John Barchi, Jr., Frederick, MD (US); Michael Bustin, Rockville, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 318 days.

(21) Appl. No.: 16/313,454

(22) PCT Filed: Feb. 24, 2017

(86) PCT No.: PCT/US2017/019342
§ 371 (c)(1),
(2) Date: Dec. 26, 2018

(87) PCT Pub. No.: WO2018/004747
PCT Pub. Date: Jan. 4, 2018

(65) Prior Publication Data
US 2019/0151466 A1    May 23, 2019

Related U.S. Application Data

(60) Provisional application No. 62/355,134, filed on Jun. 27, 2016.

(51) Int. Cl.
| | |
|---|---|
| *A61K 47/69* | (2017.01) |
| *A61K 9/51* | (2006.01) |
| *A61K 39/395* | (2006.01) |
| *C07K 16/28* | (2006.01) |
| *A61K 31/664* | (2006.01) |
| *C07D 215/00* | (2006.01) |
| *A61K 45/06* | (2006.01) |
| *A61K 38/17* | (2006.01) |
| *A61P 35/00* | (2006.01) |
| *A61K 9/00* | (2006.01) |
| *A61K 31/4745* | (2006.01) |
| *A61K 47/02* | (2006.01) |
| *B82Y 5/00* | (2011.01) |

(52) U.S. Cl.
CPC ........ *A61K 47/6929* (2017.08); *A61K 9/0019* (2013.01); *A61K 9/51* (2013.01); *A61K 9/5115* (2013.01); *A61K 31/4745* (2013.01); *A61K 31/664* (2013.01); *A61K 38/1709* (2013.01); *A61K 39/39558* (2013.01); *A61K 45/06* (2013.01); *A61K 47/02* (2013.01); *A61K 47/6923* (2017.08); *A61P 35/00* (2018.01); *C07K 16/2818* (2013.01); *C07K 16/2827* (2013.01); *B82Y 5/00* (2013.01)

(58) Field of Classification Search
None
See application file for complete search history.

(56) References Cited

U.S. PATENT DOCUMENTS

| 5,389,640 A | 2/1995 | Gerster et al. |
|---|---|---|
| 8,227,417 B2 | 7/2012 | Yang et al. |
| 10,517,946 B2 * | 12/2019 | Jewell ................. A61K 39/39 |
| 2006/0222595 A1 | 10/2006 | Mukherjee et al. |
| 2007/0154529 A1 | 7/2007 | Bullerdiek |
| 2010/0021488 A1 | 1/2010 | Yang et al. |

FOREIGN PATENT DOCUMENTS

| WO | WO 2004/083398 |   | 9/2004 |
|---|---|---|---|
| WO | WO 2010/003009 | * | 1/2010 |
| WO | WO 2010/003009 A2 |   | 1/2010 |
| WO | WO 2012/045090 A2 |   | 4/2012 |

OTHER PUBLICATIONS

Napolitani et al (Nature Immunology, 2005, 6:769-776).*
Yang et al (Journal of Experimental Medicine, 2012, 209:157-171).*
Wei et al (Cancer Research, 2014, 74:5989-5998).*
Yaeger et al (Journal of Cancer Therapy, 2011, 2:384-393).*
Dewan et al (Clinical Cancer Research, 2012, 18:6668-6678).*
Hilton et al (Journal for Immunotherapy of Cancer, 2014, 2(Suppl 3):p. 249).*
Hodi et al (NEJM, 2010, 363:711-723).*
Yuan et al (Cancer Immunol. Immunother., 2011, 60:1137-1146).*
Park et al (Immune Network, 2013, 13:177-183).*
Almeida et al (Nanomedicine: Nanotechnology, Biology, and Medicine, 2014, 10: 503-514).*
Stiufiuc et al (Journal of Nanomaterials, 2013, 7 pages).*
Connolly et al., "New developments in Toll-like receptor targeted therapeutics," Current Opinion in Pharmacology, 2012, 12:510-518.

(Continued)

*Primary Examiner* — Laura B Goddard
(74) *Attorney, Agent, or Firm* — Klarquist Sparkman, LLP

(57) ABSTRACT

Methods of treating cancer or reducing the incidence of relapse of a cancer in a subject comprising co-administration of Toll-like receptor (TLR) 4 ligand, such as an HMGN1 protein, and a TLR 7 or 8 ligand, and optionally an immune checkpoint inhibitor, to the subject in need of such therapy. The TLR4-mediated immune-stimulating effect is synergistically enhanced by ligands of TLR7 or 8, and the immune checkpoint inhibitor. Also described here is a nanoparticle delivery platform for the co-administration of the TLR 4 ligand and the TLR 7 or 8 ligand.

24 Claims, 24 Drawing Sheets

(56) References Cited

OTHER PUBLICATIONS

Ding et al., "Cytotoxic Chemotherapy and CD4+ Effector T Cells: An Emerging Alliance for Durable Antitumor Effects," Hindawi Publishing Corporation, Clinical and Developmental Immunology, vol. 2012, Article ID 890178, Nov. 5, 2011, 12 pages.
International Search Report from the parent PCT Application No. PCT/US2017/019342, 4 pages (dated Jun. 9, 2017).
Jain et al., "Gold nanoparticles as novel agents for cancer therapy," *British Journal of Radiology* 85(1010): 101-113 (Feb. 1, 2012).
Patil et al., "Imidazoquinolines: Recent Developments in Anticancer Activity," Mini Rev Med Chem. 2016; 16(4):309-22.
Wei et al., The Alarmin HMGN1 contributes to antitumor immunity and is a potent immunoadjuvant, *Cancer Research* 74: 5989-5998.
Written Opinion from the parent PCT Application No. PCT/US2017/019342, 9 pages (dated Jun. 9, 2017).
Yang et al., "Harnessing the alarmin HMGN1 for anticancer therapy," *Immunotherapy* 7(11): 1129-1131 (Epub Nov. 16, 2015).
Yang et al., "High-mobility group nucleosome-binding protein 1 acts as an alarmin and is critical for lipopolysaccharide-induced immune responses," *The Journal of Experimental Medicine* 209: 157-171.
Arvizo et al., "Gold nanoparticles: Opportunities and Challenges in Nanomedicine," *Expert Opin. Drug Deliv*.7(6):753-63 (2010).
Assal et al., "Emerging targets in cancer immunotherapy: beyond CTLA-4 and PD-1," *Immunotherapy* 7(11): 1169-1186 (2015).
Dreaden et al., "Size matters: gold nanoparticles in targeted cancer delivery," *Therapeutic Deliver.* 3(4):457-58 (2012).
Jokerst et al., "Nanoparticle PEGylation for imaging and therapy," *Nanomedicine* 6(4):715-28 (2011).
Khan et al., "Kinetics of protein adsorption on gold nanoparticles with variable protein structure and nanoparticle size," *Journal of Chem. Phys.* 143916);164709 (2015) (abstract only).
Oppenheim, "Kiel Talk: Development of an Immunotherapeutic Regiment for Tumors," *Cellular Immunology Section Laboratory of Molecular Immunoregulation, National Cancer Institute*, (print-out of slides from oral presentation on Nov. 3, 2015).
Pardoll, "The blockade of immune checkpoints in cancer immunotherapy," *Nature Reviews Cancer* 12, 252-264 (Apr. 2012).
Postnikov et al., "Loss of the nucleosome-binding protein HMGN1 affects the rate of N-nitrosodiethylamine induced hepatocarcinogenesis in mice," *Mol. Cancer Res.* 12(1): 82-90 (2014).
Han et al., "Therapeutic vaccine to cure large mouse hepatocellular carcinomas," Oncotarget, 2017, 8.32:52061-52071.
Nie et al., "Development of a Curative Therapeutic Vaccine (TheraVac) for the Treatment of Large Established Tumors," Scientific Reports, 2017, 7:14186 (12 pages).

\* cited by examiner

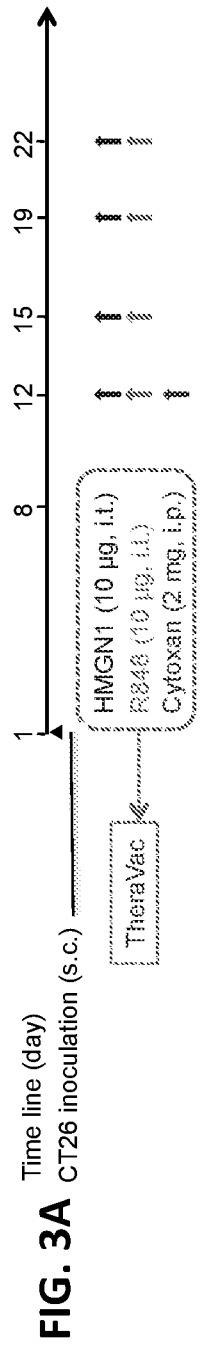
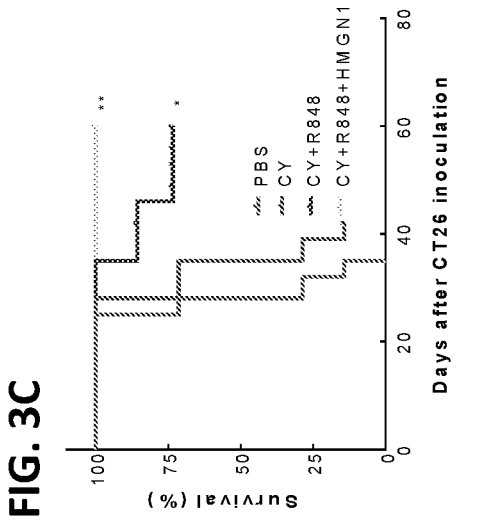
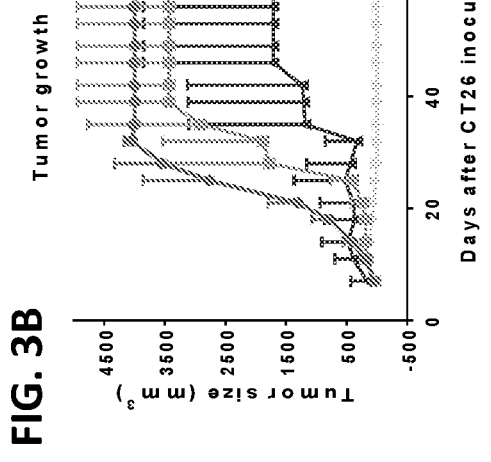
FIG. 3A
FIG. 3B
FIG. 3C

○ No CT26 tumor    ○ 4T1 tumors formed

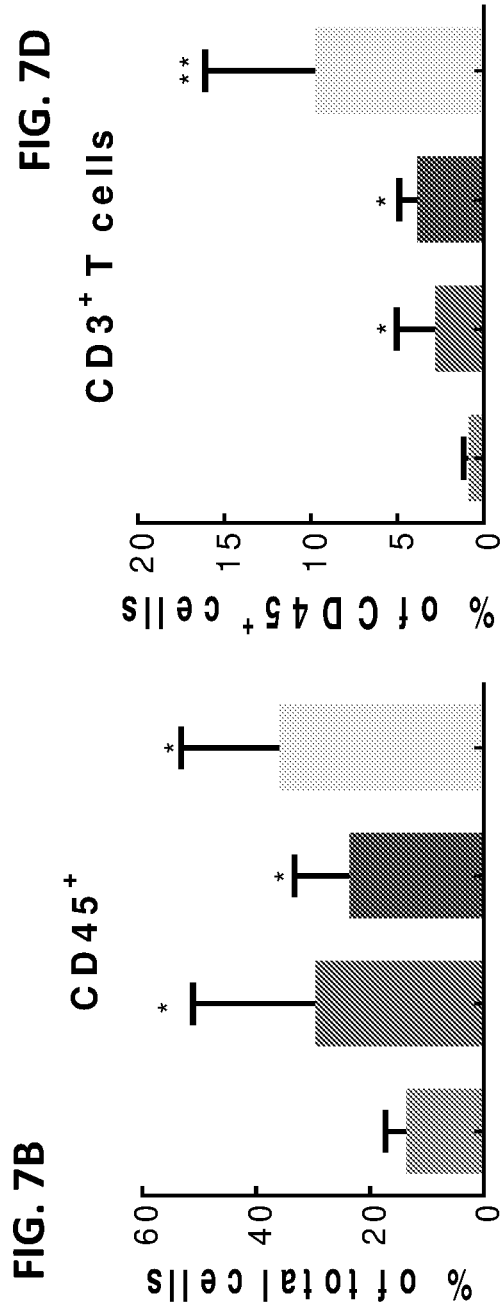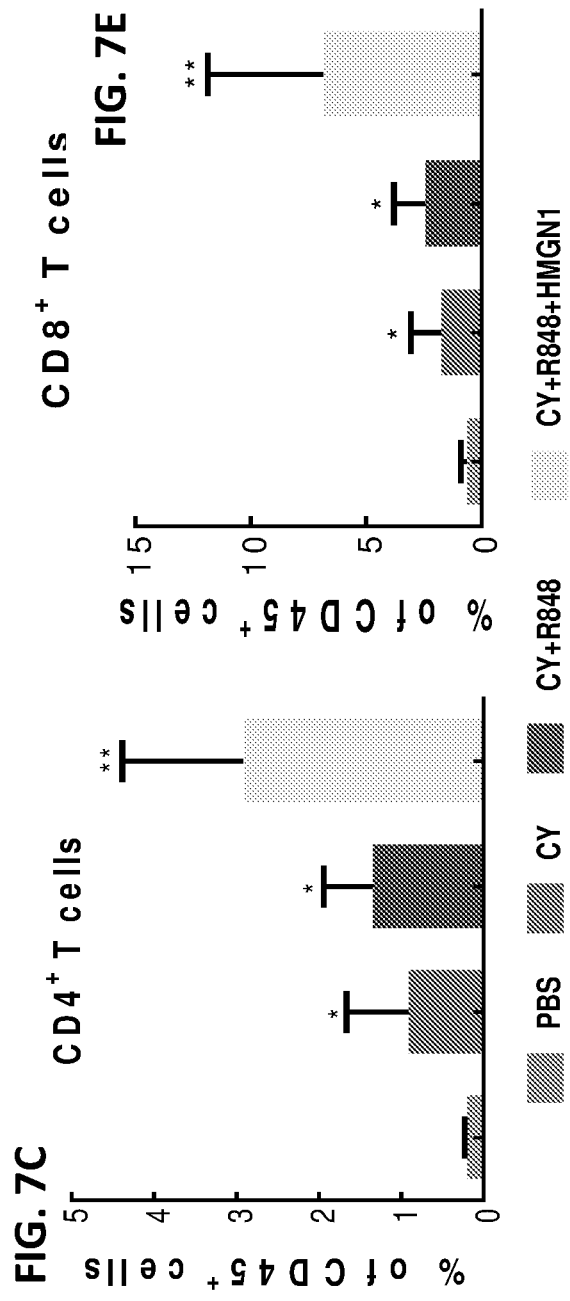

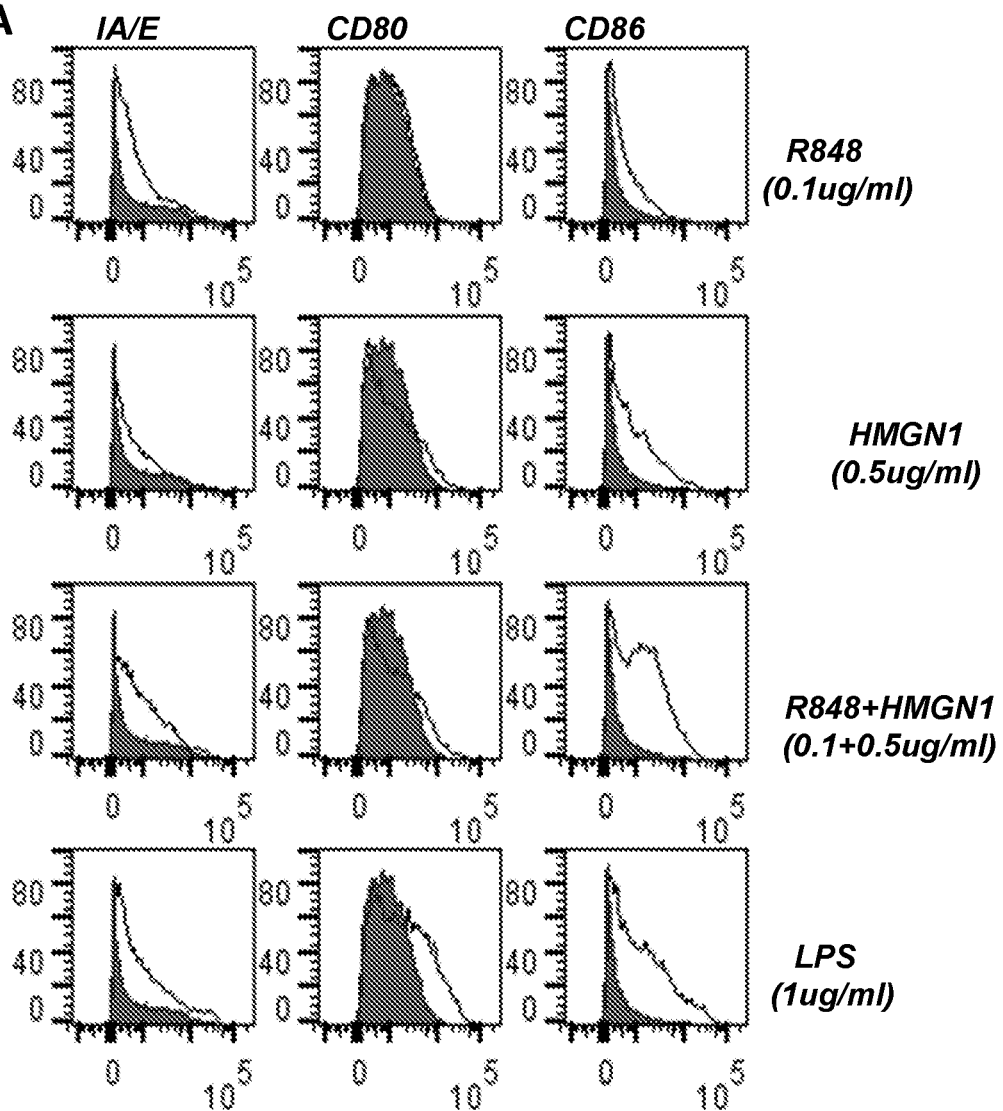

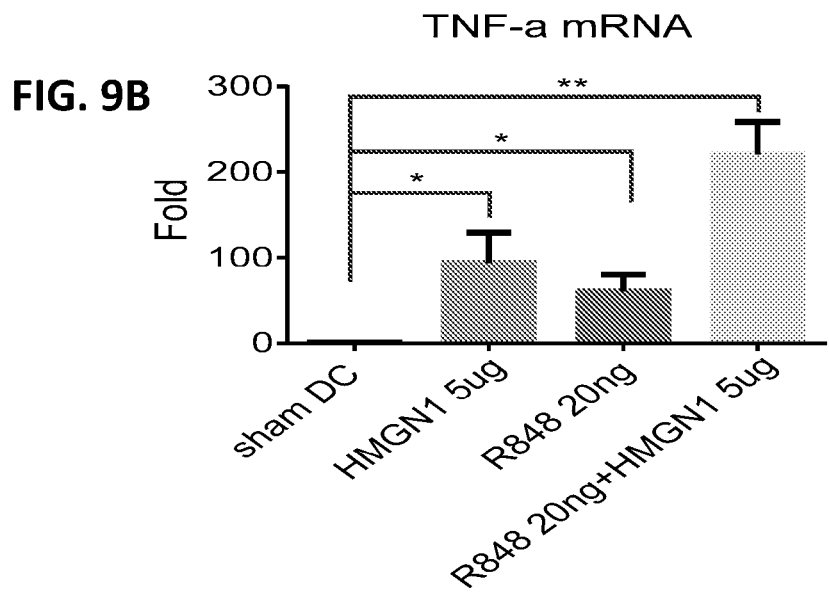
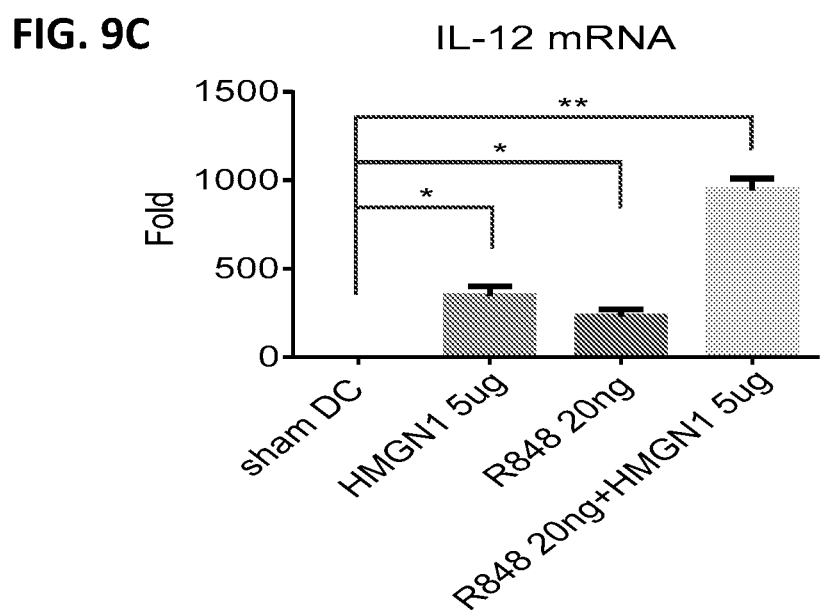

Flow chart of Au-PEG-HMGN1-R848 generation.

Sample preparation

HMGN1: 1ug
Au-PEG-N1: incubate with PEG, then add HMGN1
Au-PEG-N1-R848: incubate with PEG, then add HMGN1 and R848 at the same time Boil for 5 min → Cool down abruptly → Spin at 15,000×g for 5 min → Load onto a 4~12% gradient gel

Result: Most of the HMGN1 was contained in the Au-PEG-HMGN1-R848 complex by Western Blot analysis.

Result: About 60% of R848 was contained in the Au-PEG-HMGN1-R848 complex.

Au-PEG-HMGN1-R848 complex was stable in RPMI1640 and mouse serum for over 1 month.

Result: Au-PEG-HMGN1-R848 stimulated the maturation of human DCs by upregulating CD83, CD86, HLA-DR and CD80.

Result: The accumulation of Au-PEG-HMGN1-R848 was evidenced by a marked change in the color of the organs or tumor.

Result: Intratumor injection cured 5/5 mice, while intravenous treatment with the Au-PEG-HMGN1-R848 nanoparticles along with cyclophosphamide cured 3/5 mice.

FIG. 17     DLS Data---Au-PEG-HMGN1-R848
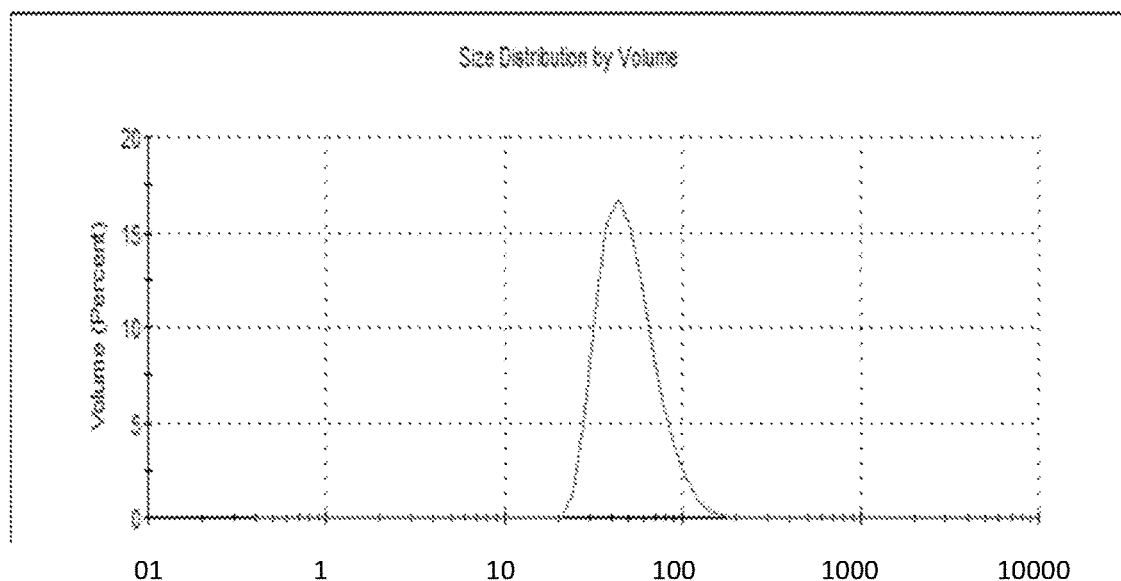

FIG. 18      Zeta Potential Data---Au-PEG-HMGN1-R848

Sample Name: Au_PEG_HMGN1_R848_TheR848Set 1
SOP Name: mansettings.nano
File Name: HMGN1_R848_DLS_June2016.dts
Record Number: 24
Date and Time: Friday, July 01, 2016 10:11:59 AM Dispersant Name: Water
Dispersant RI: 1.330
Viscosity (cP): 0.8872
Dispersant Dielectric Constant: 78.5

Temperature (°C): 25.0
Count Rate (kcps): 135.4
Cell Description: Clear disposable zeta cell Zeta Runs: 14
Measurement Position (mm): 2.00
Attenuator: 10

|  | Mean (mV) | Area (%) | St Dev (mV) |
|---|---|---|---|
| Zeta Potential (mV): -6.72 | Peak 1: -5.69 | 99.9 | 11.4 |
| Zeta Deviation (mV): 11.5 | Peak 2: -48.9 | 0.1 | 1.66 |
| Conductivity (mS/cm): 0.0460 | Peak 3: 0.00 | 0.0 | 0.00 |

Result quality : See result quality report

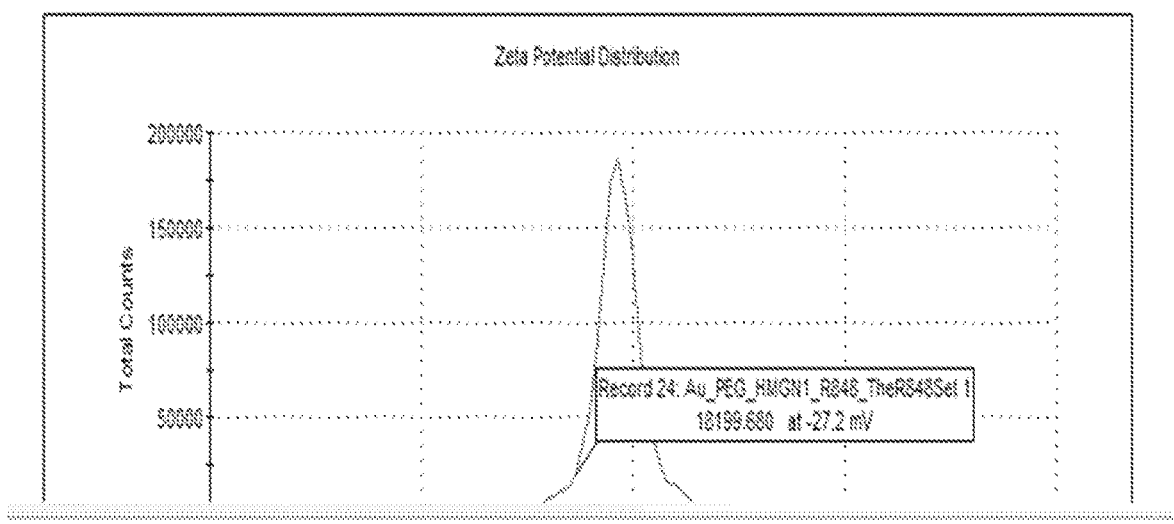

THERAPEUTIC ANTITUMOR COMBINATION OF A TLR4 LIGAND WITH OTHER TREATMENTS

CROSS REFERENCE TO RELATED APPLICATION

This is a § 371 U.S. national stage of International Application No. PCT/US2017/019342, filed Feb. 24, 2017, which was published in English under PCT Article 21(2), which claims the benefit of U.S. Provisional Application Ser. No. 62/355,134, filed Jun. 27, 2016, which is incorporated herein by reference in its entirety.

TECHNICAL FIELD

This disclosure relates to anti-cancer therapy including the administration of a Toll-like receptor (TLR) 4 ligand, such as High Mobility Group Nucleosome-binding protein 1 (HMGN1), combined with a TLR 7 or 8 ligand, and optionally other agents, such as an immune check point inhibitor.

BACKGROUND

The High Mobility Group (HMG) family of chromosomal binding peptides are subdivided into three subfamilies, each of which has a characteristic functional sequence motif: HMGB (HMG-box motif), HMGN (nucleosomal binding domain), and HMGA (AT-hook motif). HMGN polypeptides include HMGN1 (high mobility group nucleosome-binding protein 1; formerly known as HMG14), HMGN2, HMGN3a, HMGN3b, HMGN4, and Nsbp1(NBD-45).

HMGN1 has a combination of activities that potentially counter the mutagenic and immunosuppressive properties of cancers. HMGN1 is a chromatin-binding nuclear protein and can also act as an extracellular alarmin. Alarmins are structurally diverse endogenous cytokine-like host defense signals, which rapidly alert host defenses and enhance both innate and adaptive immune responses and exhibit potent in vivo immunoadjuvant activity. Thus, HMGN1 acts as a chromatin modifier to regulate chromatin structure, gene expression and post-translational modification of core histones, all of which are factors that affect DNA repair and tumor progression. It also possesses chemotactic activities for immune cells and activates dendritic cell (DC) maturation by interacting with TLR4. It is known to have immunostimulating effects and has been shown to enhance Th1 immune responses to antigens (Yang et al. 2012, J Exp Med. 209(1):157-71; Yang et al. (2015) *Immunotherapy* 7(11): 1129-31).

These biological activities of HMGN1 can be harnessed as antitumor activities. Mice immunized prophylactically with a combination of HMGN1 and the melanoma tumor antigen gp100, become resistant to a subsequent challenge with B16 melanoma tumor cells (Wei et al. 2014 Cancer Res; 74(21); 5989-98). This result, together with observations showing that HMGN1 knockout mice exhibit more rapid EG7/EL4 tumor growth than normal mice, suggested that HMGN1 could promote host antitumor responses. However, it has not been shown whether HMGN1, either alone or in combination with other therapeutic agents, could be used therapeutically to treat pre-existing tumors.

There is a need in the art for safer, more effective treatments for cancer which is satisfied by the present technology.

SUMMARY

This disclosure provides methods of treating cancer comprising co-administration of a Toll-like receptor (TLR) 4 ligand and a TLR7 or 8 ligand to a subject in need of such therapy. This disclosure also provides methods of reducing the incidence of relapse of a tumor comprising co-administration of a TLR4 and a TLR7 or 8 ligand to a subject having the tumor. This disclosure also provides a composition comprising a TLR4 ligand and a Toll-like receptor (TLR) 7 or 8 ligand adsorbed to a nanoparticle.

The TLR4 ligand may be selected from an HMGN1 protein, bacterial lipopolysaccharide (LPS), bacterial lipopolysaccharide (LPS), mono-phosphoryl lipid A, CD138, α-crystallin A chain, β-defensin 2, endoplasmin, fibrinogen, fibronectin, heparan sulphate, HSP22, HSP72, HSP96, OxPAPC, resistin, S100 proteins, surfactant protein A, synthetic mimetics of TLR4 agonist (including, for example, neoseptins), HMGB-1, granulysin, lactoferrin, tenascin-C, and a combination thereof. In example embodiments, the TLR4 ligand may be HMGN1 protein.

These methods may further comprise the administration of an immune checkpoint inhibitor to the subject. The methods may comprise co-administration of a TLR4 ligand, a TLR7 or TLR8 ligand, and an immune checkpoint inhibitor. In example embodiments, the methods may comprise or consist essentially of co-administration of HMGN1 protein, a TLR7 or TLR8 ligand, and an immune checkpoint inhibitor. In these methods, the TLR 4 ligand such as the HMGN1 protein, TLR7 or TLR8 ligand, and immune checkpoint inhibitor may be administered in the absence of a tumor antigen.

The TLR7 or TLR8 ligand may be selected from resiquimod, imiquimod, an imidazoquinoline derivative, 852A, VTX1463, AZD8848, ANA773 and a combination thereof. The immune checkpoint inhibitor may be selected from i) cyclophosphamide, ii) an antibody selected from anti-CTLA4, anti-PD1, anti-PDL1, anti-PDL2, anti-LAG-3, anti-BTLA, anti-B7H3, anti-B7H4, anti-TIM3, and an anti-A2aR antibody, and iii) combinations of i) and ii).

These methods may include co-administration of the TLR4 ligand such as the HMGN1 protein and the TLR7 or TLR8 ligand, with cyclophosphamide or with an anti-CTLA antibody.

In example embodiments, the methods consist of co-administration of the HMGN1 protein, resiquimod, and cyclophosphamide. The cyclophosphamide may be administered to the patient at a dose of about 100 mg/kg or less.

In further example embodiments, these methods may include co-administration of the HMGN1 protein, resiquimod, and an anti-CTLA antibody.

In these methods, the cancer may be a solid tumor. In example embodiments, the cancer may be thymoma, colon cancer, kidney cancer, and liver cancer.

In these methods the administration(s) may include intratumoral, intraperitoneal, intravenous, or intramuscular injection of at least the TLR4 ligand such as the HMGN1 protein. The HMGN1 protein may be administered by intratumoral injection. The HMGN1 protein and the TLR7 or TLR8 ligand may be administered sequentially or simultaneously. Alternatively or additionally, the HMGN1 protein and the TLR7 or TLR8 ligand may be administered in the absence of a tumor antigen.

In some embodiments, the TLR4 ligand such as the HMGN1 protein and the TLR7 or TLR8 ligand are administered simultaneously. This administration may be by means of a nanoparticle adsorbed with the TLR4 ligand (such as the HMGN1 protein) and the TLR 7 or 8 ligand. Thus, in some embodiments, the methods include administering a composition comprising a nanoparticle adsorbed with the HMGN1 protein and the TLR 7 or 8 ligand.

In some embodiments, the nanoparticle may be PEGylated. In some embodiments, the nanoparticle may have an average diameter of between about 10 nm and about 100 nm, or between about 30 nm and about 70 nm, or about 50 nm. In some embodiments, the nanoparticle may have an average zeta potential between about −40 mV and about +40 mV, between about −20 mV and about +20 mV, or between about −10 mV and about +10 mV, or about −7 mV.

In some embodiments, the composition may comprise between about 70% and about 96% gold, or between about 73% and about 93% gold, or between about 78% and about 88% gold, or about 83% gold. In some embodiments, the composition may comprise between about 2% and about 22% PEG, or between about 5% and about 19% PEG, or between about 8% and about 16% PEG, or about 12% PEG. In some embodiments, the composition may comprise between about 0.5% and about 10% HMGN1 protein, or between about 1% and about 9% HMGN1 protein, or between about 2% and about 8% HMGN1 protein, or about 2.9% HMGN1 protein. In some embodiments, the composition may comprise between about 0.5% and about 10% TLR 7 or 8 ligand, or between about 1% and about 9% TLR 7 or 8 ligand, or between about 2% and about 8% TLR 7 or 8 ligand, or about 2.1% TLR 7 or 8 ligand. In some embodiments, the composition may comprise between about 70% and about 96% gold, between about 2% and about 22% PEG, between about 0.5% and about 10% HMGN1 and between about 0.5% and about 10% TLR 7 or 8 ligand. In some embodiments, the composition may comprise between about 78% and about 88% gold, between about 7% and about 17% PEG, between about 0.5% and about 6% HMGN1 and between about 0.5% and about 6% TLR 7 or 8 ligand. In some embodiments, the ratio of gold:PEG:HMGN1:TLR 7 or 8 ligand in the composition may be about 83:12:3:2.1.

In some embodiments, the TLR7 or TLR8 ligand may be selected from resiquimod, imiquimod, an imidazoquinoline derivative, 852A, VTX1463, AZD8848, and a combination thereof. In some embodiments, the TLR7 or TLR8 ligand may be selected from resiquimod, In some embodiments, the present invention includes a composition comprising an HMGN1 protein and a Toll-like receptor (TLR) 7 or 8 ligand adsorbed to a nanoparticle. In some embodiments, the composition may further comprise an immune checkpoint inhibitor selected from the group consisting of i) cyclophosphamide, ii) an antibody selected from anti-CTLA4, anti-PD1, anti-PDL1, anti-PDL2, anti-LAG-3, anti-BTLA, anti-B7H3, anti-B7H4, anti-TIM3, and an anti-A2aR antibody, and iii) combinations of i) and ii). In some embodiments, the immune checkpoint inhibitor may be selected from cyclophosphamide or an anti-CTLA antibody. In some embodiments, the composition is in an amount effective for treating cancer or reducing the incidence of relapse of a cancer in a subject.

BRIEF DESCRIPTION OF THE DRAWINGS

FIG. 1A is a schematic presentation of a treatment regimen, in which mice were inoculated with CT26 cells and subsequently treated as indicated. FIG. 1B is a graph depicting tumor growth over time, in which tumor size is plotted against days after inoculation, and FIG. 1C is a graph depicting the percent survival over time, for each treatment.

FIG. 2A is a schematic presentation of treatment regimen, in which mice were inoculated with CT26 cells and subsequently treated as indicated. FIG. 2B is a graph depicting tumor growth over time, in which tumor size is plotted against days after inoculation, for each treatment. FIGS. 2C and 2D are graphs depicting that the cured mice, when re-challenged with 4T1 tumor cells in the right flank and CT26 cells into the left flank, developed 4T1 tumors, but not CT26 tumors.

FIGS. 3A-3C show that administration of combination of HMGN1, R848, and Cytoxan (collectively "TheraVac") completely eradicated big (about 1 cm diameter), established CT26 tumors. FIG. 3A is a schematic presentation of treatment regimen, in which mice were inoculated with CT26 cells and subsequently treated as indicated. FIG. 3B shows tumor growth over time and representative images of tumor-bearing mice of differently treated groups on day 21 after CT26 cells inoculation. FIG. 2C is a graph depicting the percent survival over days, for each treated group. Compared with PBS group: $p<0.05$; $p<0.01$. Data of one experiment representative of three are shown.

FIG. 4A shows no formation of CT26 tumors in the right flank of three representative mice. FIG. 4B shows the development of 4T1 tumors in the left flank of three representative mice with no formation of CT26 tumors in the right flank. FIGS. 4C and 4D show tumor size and tumor incidence, respectively, plotted against days after inoculation upon 4T1 re-challenge, CT26 re-challenge, and CT26 inoculation.

FIG. 5A is a schematic presentation of treatment regimen, in which mice were inoculated with RENCA cells and subsequently treated as indicated. FIG. 5B is a graph depicting RENCA tumor growth over time, in which tumor size is plotted against days after inoculation. FIG. 5C is a graph depicting the percent survival over time, for each treatment. Compared with PBS group: *$p<0.001$. Data of one experiment representative of two are shown.

FIG. 6A is a schematic presentation of treatment regimen, in which mice were inoculated with CT26 cells and subsequently treated as indicated. FIGS. 6B-6D show the percent of plasmacytoid dendritic cells, Myeloid dendritic cells, and macrophages, respectively, in the tumors of each treated group. Shown are the average (Mean±SEM) of three mice of each group in one experiment representative of two. Compared with PBS group, *$p<0.05$, **$p<0.01$.

FIGS. 7A-7E show that administration of TheraVac increased the number of T cells in the tumor tissue. FIG. 7A is a schematic presentation of the treatment regimen, in which mice were inoculated with CT26 cells and subsequently treated as indicated. FIGS. 7B-7E show the percentage of $CD45^+$, $CD4^+$, $CD3^+$, and $CD8^+$ T cells, respectively, in the tumors of each treated group. Shown are the average (Mean±SEM) of three mice of each group in one experiment representative of two. Compared with PBS group, *$p<0.05$, **$p<0.01$.

FIG. 8A is a schematic presentation the of administration regimen, in which mice were inoculated with CT26 cells and subsequently treated as indicated. FIG. 8B is a graph depicting tumor growth over time, in which tumor size is plotted against days after inoculation, and FIG. 8C is a graph depicting the percent survival over time, for each treatment.

FIGS. 9A-9C show that the combination of HMGN1 and R848 have synergistic effects on dendritic cell (DC) activation, and expression of TNF-alpha and IL-12. FIG. 9A shows representative FACS profiles for IA/E, CD80, and CD86 obtained with R848 alone, HMGN1 alone, or the combination of R848 and HMGN1 and LPS. FIGS. 9B and 9C represent TNF-α and IL-12 mRNA expression levels obtained with each treatment.

FIG. 10 is a graph depicting Hepa 1-6 tumor growth over time, in which tumor volume is plotted against days after inoculation.

FIG. 12A presents a flowchart for the process of preparing Au-PEG-HMGN1-R848 nanoparticles. FIG. 12B shows a Western Blot confirming the presence of HMGN1 in the Au-PEG-HMGN1-R848 complex. FIG. 12C shows the absorbance of the total R848 (4.29) and the supernatant containing unadsorbed R848 (1.38) at 320 nm (A(320)) using a NanoDrop spectrophotometer showing that more than 60% of R848 was contained in the Au-PEG-HMGN1-R848 complex. FIG. 12D shows that the Au-PEG-HMGN1-R848 complex was stable in RPMI 1640 medium and mouse serum for over 1 month.

FIG. 17 shows DLS data of Au-PEG-HMGN1-R848 nanoparticles.

FIG. 18 shows zeta potential data of Au-PEG-HMGN1-R848 nanoparticles.

DETAILED DESCRIPTION OF THE EMBODIMENTS

Figure 1A:
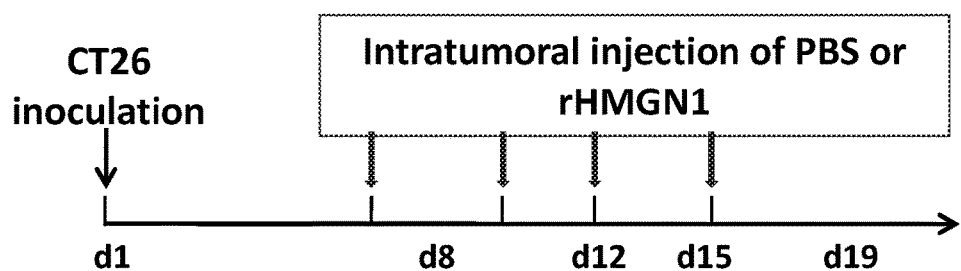
FIGS. 1A-1C show that the administration of HMGN1 protein partially inhibited growth of small (about 0.5 cm) CT26 tumors.

Described herein are anti-cancer therapeutic compositions, and methods based on the administration of such compositions to a subject in need thereof. These compositions include a TLR4 ligand, such as High Mobility Group Nucleosome-binding protein 1 (HMGN1) protein. As shown in Example 1 of this disclosure, administration of HMGN1 suppressed the growth of pre-existing, solid tumors in mice in a dose-dependent manner. Furthermore, this therapeutic effect did not require co-administration of an antigen. Without wishing to be bound by theory, the present inventors propose that HMGN1 binds to Toll-like receptor (TLR) 4 and, by activating dendritic cells, augments the generation of antitumor immunity. The TLR4-mediated immunostimulating effect of HMGN1 is enhanced by the administration of activators of TLR7 or 8 in a synergistic manner. Furthermore, as described in greater detail below, co-administration of HMGN1 and a TLR7 or TLR8 ligand along with an immune checkpoint inhibitor resulted in an even greater synergistic anti-cancer therapeutic effect.

Because HMGN1 is a potent TLR4 ligand with agonistic effects, other TLR4 ligands are expected to also be effective in synergizing with TLR7 or 8 ligands. Examples of other TLR4 ligands suitable for use in the present invention include, without limitation, bacterial lipopolysaccharide (LPS), mono-phosphoryl lipid A, CD138, α-crystallin A chain, β-defensin 2, endoplasmin, fibrinogen, fibronectin, heparan sulphate, HSP22, HSP72, HSP96, OxPAPC, resistin, S100 proteins, surfactant protein A, synthetic mimetics of TLR4 agonist (including, for example, neoseptins), HMGB-1, granulysin, lactoferrin, and tenascin-C.

Thus, this disclosure provides methods of treating cancer in a subject comprising administering to the subject a TLR4 Ligand and a TLR7 or 8 ligand. These methods may comprise administering to the subject HMGN1 protein and a TLR7 or 8 ligand.

The amino acid sequence of HMGN1 is known in the art, and is disclosed in U.S. Pat. No. 8,227,417, which is incorporated herein by reference. The term HMGN1 protein refers to the full length protein or a polypeptide comprising a functional fragment thereof. These proteins can be obtained by methods known in the art. For example, suitable methods of de novo synthesis of proteins or polypeptides are described in, e.g., Chan et al., Fmoc Solid Phase Peptide Synthesis, Oxford University Press, Oxford, United Kingdom, 2005; Peptide and Protein Drug Analysis, ed. Reid, R., Marcel Dekker, Inc., 2000; Epitope Mapping, ed. West Wood et al., Oxford University Press, Oxford, United Kingdom, 2000; and U.S. Pat. No. 5,449,752.

These proteins can also be recombinantly-produced using nucleic acids encoding them and standard recombinant methods. See, for example, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, NY, 1994. Further, these proteins can be isolated and/or purified from a natural source, e.g., a human. Methods of isolation and purification are well-known in the art. In this respect, the HMGN1 protein (including polypeptides comprising a functional fragment thereof) may be exogenous and may be synthetic, recombinant, or of natural origin. HMGN1 protein is also commercially available (e.g., R&D Systems Inc., Minneapolis, Minn.).

Functional fragments of the HMGN1 protein may comprise any contiguous part of the HMGN1 protein that retains a relevant biological activity of the HMGN1 protein. Any given fragment of an HMGN1 protein can be tested for such biological activity using methods known in the art (see, for example, U.S. Pat. No. 8,227,417, which is incorporated herein by reference). The functional fragment may comprise, for instance, about 10% or more, 25% or more, 30% or more, 50% or more, 60% or more, 80% or more, 90% or more, 95% or more, or even 97% or more of the full length HMGN1 amino acid sequence. The HMGN1 protein (including polypeptides comprising a functional fragment thereof) may be glycosylated, amidated, carboxylated, phosphorylated, esterified, N-acylated, cyclized via, e.g., a disulfide bridge, or converted into an acid addition salt and/or optionally dimerized or polymerized, or conjugated. Suitable pharmaceutically-acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid. The methods of the invention may comprise administering two or more HMGN1 polypeptides, any of which may be the same or different from one another. Furthermore, the HMGN1 protein, or functional fragment thereof, can be provided as part of a larger polypeptide construct. For instance, the HMGN1 protein or functional fragment thereof can be provided as a fusion protein comprising an HMGN1 polypeptide or functional fragment along with other amino acid sequences or a nucleic acid encoding the same. By way of further illustration, the HMGN1 polypeptide or functional fragment can be provided by two or more fragments of the HMGN1 protein (e.g. different functional domains) with or without a linking amino acid sequence and/or flanking sequences. The HMGN1 protein or a fragment thereof also may be provided as part of a conjugate or nucleic acid(s) encoding the same. Conjugates, as well as methods of synthesizing conjugates in general, are known in the art (See, for instance, Hudecz, F., Methods Mol. Biol. 298: 209-223 (2005); and Kirin et al., Inorg Chem. 44(15): 5405-5415 (2005)).

TLR 7 and TLR 8 are mainly expressed in intracellular vesicles such as the endoplasmic reticulum, endosomes, lysosomes and endolysosomes, where they recognize microbial nucleic acids. TLR7 and TLR8 recognize single stranded RNA (ssRNA) derived from ssRNA viruses and small molecule imidazoquinoline derivatives. A number of TLR7 or TLR8 ligands are known in the art and may be administered in the methods of the present invention. See e.g. Connolly and O'Neill, *New developments in Toll-like receptor targeted therapeutics* (2012) *Current Opinion in Pharmacology* 12:510-18. Examples of TLR7 or 8 ligands include, without limitation, resiquimod, imiquimod, an imidazoquinoline derivative, 852A, VTX1463, and AZD8848. U.S. Pat. No. 5,389,640 describes 1-substituted-, and 2-substituted-1H-imidazo[4,5-c]-quinolin-4-amines including the compound resiquimod (R-848; (1H-Imidazo(4,5-c)quinoline-1-ethanol(ethoxymethyl)-alpha, alpha-dimethyl). Resiquimod is a dual TLR7/TLR8 agonist. The compounds imiquimod, 852A, AZD8848 and ANA773 are known to be agonists of TLR7, whereas VTX1463 is an agonist of TLR8. Use of all TLR7 and TLR8 ligands, including those not listed here or those whose activity has not been recognized yet, are encompassed within the present invention.

These methods may include the co-administration of an immune checkpoint inhibitor. Treatment with a triple combination of HMGN1, a TLR 7 or 8 ligand, and an immune checkpoint inhibitor may be referred to as "TheraVac" throughout this disclosure.

Immune checkpoints refer to a plethora of pathways hardwired into the immune system that are crucial for maintaining self-tolerance (i.e., prevention of auto-immunity) and modulating the duration and amplitude of physiological immune responses in peripheral tissues in order to minimize tissue damage. The expression of immune-checkpoint proteins is dysregulated by tumors as an important immune resistance mechanism. The inhibition of immune checkpoints facilitates antitumor immune response. Because many of the immune checkpoints are initiated by ligand-receptor interactions, they can be readily inhibited by antibodies or modulated by recombinant forms of ligands or receptors. A number of immune checkpoint inhibitors are known in the art. See e.g. Pardoll et al., *The blockade of immune checkpoints in cancer immunotherapy* (2012) Nature Reviews Cancer 12:252-64; and Ding et al., *Cytotoxic Chemotherapy and CD4+ Effector T Cells: An Emerging Alliance for Durable Antitumor Effects* (2012) Clinical and Developmental Immunology 2012:1-12. Examples of immune checkpoint inhibitors include antibodies that block immune checkpoints (e.g. by targeting lymphocyte receptors or their ligands) or drug molecules that have a similar mechanism of action.

As used herein, the term "antibody" refers to an immunoglobulin molecule capable of binding an epitope present on an antigen. The term is intended to encompass not only intact immunoglobulin molecules such as monoclonal and polyclonal antibodies, but also antibody derivatives or fragments, including bi-specific antibodies, humanized antibodies, chimeric antibodies, anti-idiopathic (anti-ID) antibodies, single-chain antibodies, Fab fragments, F(ab') fragments, fusion proteins and any modifications of the foregoing that comprise an antigen recognition site of the required specificity. Many of such antibodies are already known and/or available for purchase from commercial sources. The antibodies of the invention may also be prepared by any suitable means known in the art. For example, antibodies may be prepared by immunizing an animal host with the marker or an immunogenic fragment thereof (conjugated to a carrier, if necessary). Adjuvants (e.g., Freund's adjuvant) optionally may be used to increase the immunological response. Sera containing polyclonal antibodies with high affinity for the antigenic determinant can then be isolated from the immunized animal and purified. Alternatively, antibody-producing tissue from the immunized host can be harvested and a cellular homogenate prepared from the organ can be fused to cultured cancer cells. Hybrid cells which produce monoclonal antibodies specific for a marker can be selected. Alternatively, the antibodies of the invention can be produced by chemical synthesis or by recombinant expression. For example, a polynucleotide that encodes the antibody can be used to construct an expression vector for the production of the antibody. The antibodies of the present invention can also be generated using various phage display methods known in the art.

Examples of immune checkpoint inhibitor antibodies include, without limitation, anti-CTLA4, anti-PD1, anti-PDL1, anti-PDL2, anti-LAG-3, anti-BTLA, anti-B7H3, anti-B7H4, anti-TIM3, and anti-A2aR antibodies. Examples of immune checkpoint inhibitors also include, without limitation, drugs such as cyclophosphamide, which can preferentially deplete tolerogenic CD8+ lymphoid-resident DCs, leading to diminished Treg suppression and enhanced effector T-cell function.

Thus, the methods of this disclosure may comprise co-administration of HMGN1 protein, a TLR7 or TLR8 ligand, and an immune checkpoint inhibitor. The method may consist essentially of co-administration of HMGN1 protein, a TLR7 or TLR8 ligand, and an immune checkpoint inhibitor. The method may consist of co-administration of HMGN1 protein, a TLR7 or TLR8 ligand, and an immune checkpoint inhibitor. In these embodiments, the immune checkpoint inhibitor may be an anti-CTLA antibody or the drug cyclophosphamide.

The HMGN1 protein and a TLR7 or TLR8 ligand, optionally along with an immune checkpoint inhibitor, may be administered in the absence of a tumor antigen. As described herein, despite the absence of antigen, the administration of these components showed a surprisingly robust, synergistic therapeutic effect, resulting in treating or curing or eradicating large (about 1 cm), established solid tumors.

The methods of this disclosure may be useful in the treatment of a variety of cancers. Exemplary cancers that may be treated or prevented include thymoma, acute lymphocytic cancer, acute myeloid leukemia, alveolar rhabdomyosarcoma, bone cancer, brain cancer, breast cancer, cancer of the anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, uterine cancer, esophageal cancer, cervical cancer, gastrointestinal carcinoid tumor, lymphoid and other hematopoietic tumors, Hodgkin lymphoma, B cell lymphoma, bronchial squamous cell cancer, hypopharynx cancer, kidney cancer, larynx cancer, liver cancer, pancreatic cancer, carcinoma, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. In example embodiments, the cancer may be colon cancer, kidney cancer, liver cancer, skin cancer or melanoma, breast cancer, cervical cancer, colorectal cancer, endometrial cancer, head and neck cancer, lung cancer, carcinoid, lymphoma or glioma. In exemplary embodiments, the cancer is thymoma, colon cancer, kidney cancer, or liver cancer.

In an exemplary embodiment, the administration includes the HMGN1 protein, resiquimod (R848), and cyclophosphamide (together "TheraVac"). As described in Examples 3 and 5 of this disclosure, administration of TheraVac resulted in the eradication of large (i.e. about 1 cm in size) colon tumors (CT26) and kidney tumors (RENCA), and rendered tumor bearing mice tumor free. The combination therapy of TheraVac (HMGN1, R848 and cyclophosphamide) resulted in egress of dendritic cells pDC and Myeloid DC from tumors (see Examples 6 and 7 of this disclosure). The combination therapy of TheraVac also increased the number of T cells, including $CD45^+$, $CD3^+$, $CD4^+$ and $CD8^+$ T cells, in the tumor tissue (see Example 7).

The methods of this disclosure also include the administration of the HMGN1 protein, resiquimod (R848), and an anti-CTLA or anti-PDL1 antibody. A similar therapeutic effect against CT26 xenograft tumors, Hepa 1-6 liver and E7 thymomas was achieved by substituting anti-CTLA4 or ant-PDL1 antibodies for cyclophosphamide (see Example 8).

More than one route, such as intratumoral, intraperitoneal, intravenous, intramuscular, subcutaneous, oral, or topical may be used for administration of the components of these therapeutic combinations, and particular routes may provide more immediate and more effective responses than other routes. In exemplary embodiments, the HMGN1 protein may be administered by intratumoral injection. Alternatively or additionally, the HMGN1 protein and the TLR 7 or TLR8 ligand may be administered by intratumoral injection. In some instances, intratumoral administration, presumably based on better access to tumor antigens, may be more effective than systemic injections. Nonetheless, as shown in Example 10 of this disclosure, intratumoral injection was shown to be more effective, systemic immunity developed and distant tumors were also partially suppressed.

Further, as described in Example 4 of this disclosure, upon administration of the therapeutic combinations, mice resisted re-challenge with CT26 cells, but not 4T1 tumors (see Example 4). Thus, the administration regimens described herein result in prevention of the incidence of relapse of a tumor. Accordingly, this disclosure includes a method of reducing the incidence of relapse of a tumor in a subject comprising co-administration of an HMGN1 protein and a Toll-like receptor (TLR) 7 or 8 ligand to a subject having a tumor.

The administered compositions of this disclosure may include any suitable carrier. For example, formulations suitable for intravenous, intramuscular, subcutaneous, intraperitoneal or intratumoral administration may comprise sterile aqueous solutions of the active components. Such formulations may be prepared by dissolving the HMGN1 protein (or functional fragments thereof), and/or the additional active component(s) in water containing physiologically compatible substances such as sodium chloride (e. g. 0.1-2.0M), glycine, and the like, and having a buffered pH compatible with physiological conditions to produce an aqueous solution, and rendering said solution sterile.

In some embodiments, the components of the therapeutic combination described herein may be administered by means of a nanoparticle vehicle. Nanoparticles (NPs) are synthetic particles with dimensions ranging from one to hundreds of nanometers comprising an inorganic core surrounded by an organic layer. Nanoparticles featuring inorganic cores such as gold, silica, superparamagnetic iron oxide (SPIO) are known in the art. In cancer tissue, NPs extravasate from the leaky tumor vasculature to a higher degree than healthy tissue, and remain in the area by the enhanced permeability and retention (EPR) effect. However, there are also concerns over stability, toxicity and nonspecific binding to nontargeted or nondiseased areas which may be alleviated by appropriate PEGylation of the NPs. The selection of a PEG molecule to be used for PEGylation, for example molecular weight, length of the PEG chain, or groups present at the terminal ends (such as halo, azido, thiol or sulfo groups) as well as the attachment of the PEG to the NP surface (covalent or noncovalent) depends upon the characteristics of the NP, such as the type, size and the charge or zeta potential of the NP.

As described herein, the present inventors have successfully developed a stable and effective nanoparticle composition for delivery of the components of therapeutic combinations of this disclosure. An exemplary non-limiting embodiment is disclosed in Examples 12-14.

In this exemplary embodiment, gold nanoparticles were PEGylated and adsorbed with the TLR4 ligand HMGN1 and the TLR 7 or TLR 8 ligand resiquimod (R848). HMGN1 is a hydrophilic macromolecule, whereas resiquimod is a small hydrophobic molecule. Surprisingly, the nanoparticle composition comprising a water soluble protein and lipid soluble small drug adsorbed onto the NP surface was stable and active. The nanoparticle composition was stable in mouse sera for at least 1 month. It exhibited both in vitro and in vivo activity. It was able to induce maturation of dendritic cells and demonstrated anti-tumor activity in mice when administered in combination with an immune checkpoint inhibitor such as cyclophosphamide.

Moreover, upon intravenous administration, it was able to accumulate and persist within tumor tissue and led to potent anti-tumor activity and curative effect in mice. Thus, the nanoparticle composition may be administered systemically, and not only intratumorally, to achieve a significant therapeutic effect. Accordingly, in some embodiments, the TLR4 ligand may be administered by means of a composition comprising a nanoparticle having the TLR4 ligand adsorbed on its surface. In some embodiments, the TLR 7 or 8 ligand may be administered by means of a composition comprising a nanoparticle having the TLR4 ligand adsorbed on its surface. In some embodiments, the TLR4 ligand and the TLR 7 or 8 ligand are administered together or simultaneously via a composition comprising a nanoparticle having both the TLR4 ligand and the TLR 7 or 8 ligand adsorbed on its surface.

The nanoparticle may be a gold nanoparticle. Alternatively or additionally, the nanoparticle may be PEGylated. These nanoparticles may have an average diameter ranging from about 10 nm to about 100 nm, from about 20 nm to about 80 nm, or from about 30 nm to about 70 nm. The nanoparticles may have an average particle size of about 10 nm, 20 nm, 30 nm, 40 nm, 50 nm, 60 nm, 70 nm, 80 nm, 90 nm, or 100 nm. Exemplary nanoparticles may have an average particle size of about 50 nm.

The zeta potential value of the nanoparticles may vary from about −40 mV to about +40 mV. In some embodiments, the nanoparticles may have an average zeta potential between about −40 mV and +40 mV, between about −30 mV and +30 mV, or between about −20 mV and +20 mV, or between about −10 mV and +10 mV. Exemplary nanoparticles may have an average zeta potential of about −7 mV.

These nanoparticle compositions may contain between about 70% to about 96% gold, or about 73% to about 93% gold, or about 78% to about 88% gold. These compositions may contain about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, or 96% gold. Exemplary compositions may contain about 83% gold.

These compositions may contain about 2% to about 22% PEG, or about 5% to about 19% PEG, or about 8% to about 16% PEG. These compositions may contain about 2%, 3%, 4%, 5%, 6%, 7%, 8%, 9%, 10%, 11%, 12%, 13%, 14%, 15%, 16%, 17%, 18%, 19%, 20%, 21%, or 22% PEG. Exemplary compositions may contain about 12% PEG.

The compositions may contain between about 0.5% to about 10% HMGN1 protein, or about 1% to about 9% HMGN1 protein, or about 2% to about 8% HMGN1 protein. In some embodiments, the composition may contain about 0.5%, 1%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.5%, 5%, 5.5%, 6%, 6.5%, 7%, 7.5%, or 8% HMGN1 protein. Exemplary compositions may contain about 2.9% HMGN1 protein.

These compositions may contain about 0.5% to about 10% TLR 7 or 8 ligand, or about 1% to about 9% TLR 7 or 8 ligand, or about 2% to about 8% TLR 7 or 8 ligand. These compositions may contain about 0.5%, 1%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.5%, 5%, 5.5%, 6%, 6.5%, 7%, 7.5%, or 8% TLR 7 or 8 ligand. Exemplary compositions may contain about 2.1% TLR 7 or 8 ligand.

An exemplary composition may contain between about 70% and about 96% gold, between about 2% and about 22% PEG, between about 0.5% and about 10% HMGN1 and between about 0.5% and about 10% TLR 7 or 8 ligand. In some embodiments, the ratio of gold:PEG:HMGN1:TLR 7 or 8 ligand in the composition is about 83:12:3:2.1.

Exemplary TLR7 or TLR8 ligands may be selected from resiquimod (R848), imiquimod, an imidazoquinoline derivative, 852A, VTX1463, AZD8848, and a combination thereof. The TLR7 or TLR8 ligand may be resiquimod (R848).

This disclosure also provides kits containing the composition. The kit may include a pharmaceutically acceptable carrier and/or instructions for use of the composition in the methods described herein. For purposes of the invention, the amount or concentration of the HMGN1 protein or fragment thereof, and other active ingredients should be sufficient to effect a desired biological response, e.g., a therapeutic response, in the subject or animal using a reasonable dosage regimen over a reasonable time frame. The dose will be determined by the efficacy of the particular component and the condition of the subject (e.g., human cancer patient), as well as the body weight of the subject to be treated. The dose also will be determined by the existence, nature and extent of any adverse side effects that might accompany the administration. Typically, determination of the dosage with which to treat each individual patient is well within the grasp of the medical provider, taking into consideration a variety of factors, such as age, body weight, general health, diet, sex, route of administration, and the severity of the condition being treated.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As used in this specification and the appended claims, when the terms "one," "a," or "an" are used in this disclosure, they mean "at least one" or "one or more," unless otherwise indicated. Thus, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure, and so forth.

As used herein, the term "subject" includes, for example, humans, sheep, horses, cattle, pigs, dogs, cats, rats, mice, mammals, birds, reptiles, fish, insects and arachnids.

As used herein, the terms "treatment," "treat," "treated," or "treating" refer to prophylaxis and/or therapy. When used with respect to an infectious disease, for example, the term refers to a prophylactic treatment which increases the resistance of a subject to infection with a pathogen or, in other words, decreases the likelihood that the subject will become infected with the pathogen or will show signs of illness attributable to the infection, as well as a treatment after the subject has become infected in order to fight the infection, e.g., reduce or eliminate the infection or prevent it from becoming worse. In certain examples, the terms are meant to refer to an approach for obtaining beneficial or desired clinical results. For purposes of this disclosure, beneficial or desired clinical results include, but are not limited to, alleviation of symptoms, diminishment of extent of disease, stabilization (e.g., not worsening) of disease, preventing spread of disease, delaying or slowing of disease progression, amelioration or palliation of the disease state, and remission (partial or total) whether detectable or undetectable. In addition, "treat," "treating," and "treatment" can also mean prolonging survival as compared to expected survival if not receiving treatment.

As will be clear to those skilled in the art, embodiments of the invention may involve the use of recombinant nucleic acid technologies such as cloning, polymerase chain reaction, the purification of DNA and RNA, the expression of recombinant proteins in prokaryotic and eukaryotic cells, etc. Such methodologies are well known to those skilled in the art and can be conveniently found in published laboratory methods manuals (e.g., Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997)). Fundamental laboratory techniques for working with tissue culture cell lines (Celis, J., ed., CELL BIOLOGY, Academic Press, 2.sup.nd edition, (1998)) and antibody-based technologies (Harlow, E. and Lane, D., "Antibodies: A Laboratory Manual," Cold Spring Harbor Laboratory, Cold Spring Harbor, N.Y. (1988); Deutscher, M. P., "Guide to Protein Purification," Meth. Enzymol. 128, Academic Press San Diego (1990); Scopes, R. K., "Protein Purification Principles and Practice," 3.sup.rd ed., Springer-Verlag, New York (1994)) are also adequately described in the literature, all of which are incorporated herein by reference.

The following examples further illustrate details and embodiments of the invention but should not be construed as limiting its scope.

EXAMPLES

Standard techniques well known in the art or the techniques specifically described below were utilized.

Example 1

This example demonstrates that administration of HMGN1 prevented the growth of small (about 5 mm in diameter) established CT26 tumors.

Figure 1B:
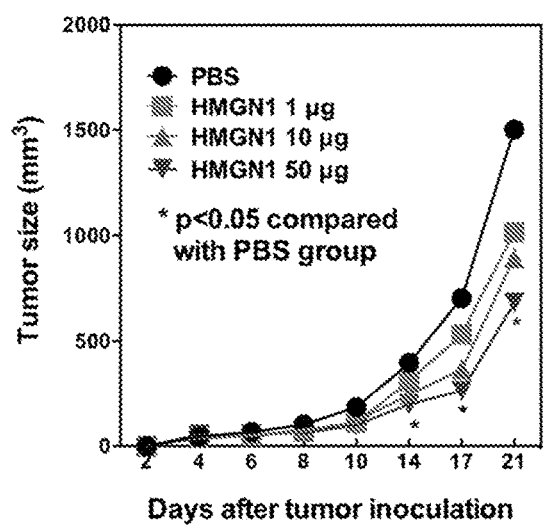
Figure 1C:
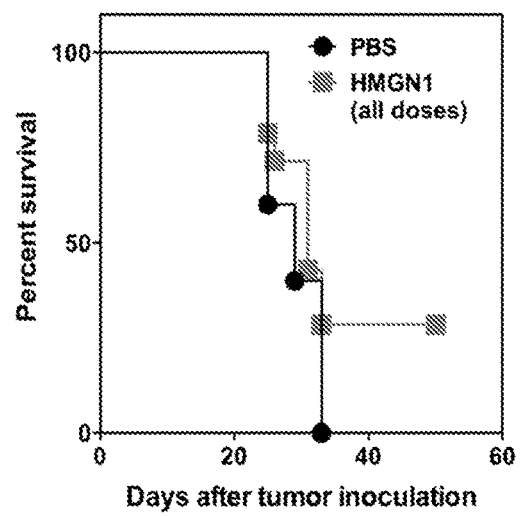

Intratrumoral injection of HMGN1 alone into small (about 5 mm diameter) CT26 tumors slowed down tumor growth, but did not completely eradicate tumors. These results are shown in FIG. 1. Balb/c mice were inoculated subcutaneously with 100,000 or 200,000 CT26 cells on day 1. Tumor-bearing mice were treated with PBS or recombinant HMGN1 as indicated in FIG. 1A. The tumor size reached approx. 5 mm in diameter by about day 4-6 after the inoculation. On days 8, 12, 15 and 19 mice were administered PBS or 1 µg, 10 µg or 50 µg of rHMGN1. Tumor growth was monitored and plotted. As shown in FIG. 1Bm treatment with HMGN1 inhibited tumor growth in a dose dependent manner. An improvement in percent survival was also observed.

Example 2

This example demonstrates that co-administration of HMGN1 and cyclophosphamide (Cytoxan or CY) prevented the growth of small (about 5 mm in diameter) established CT26 tumors.

Figure 2A:
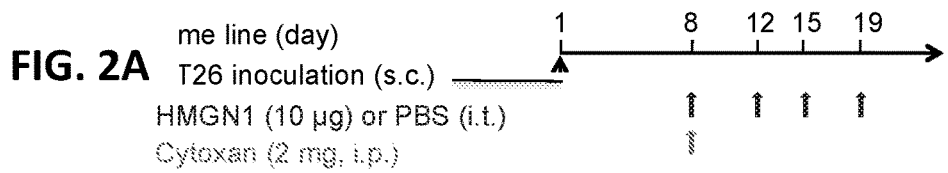
FIGS. 2A-2D show that administration of HMGN1 and Cytoxan (CY) completely inhibited growth of small (about 0.5 cm) CT26 tumors.
Figure 2B:
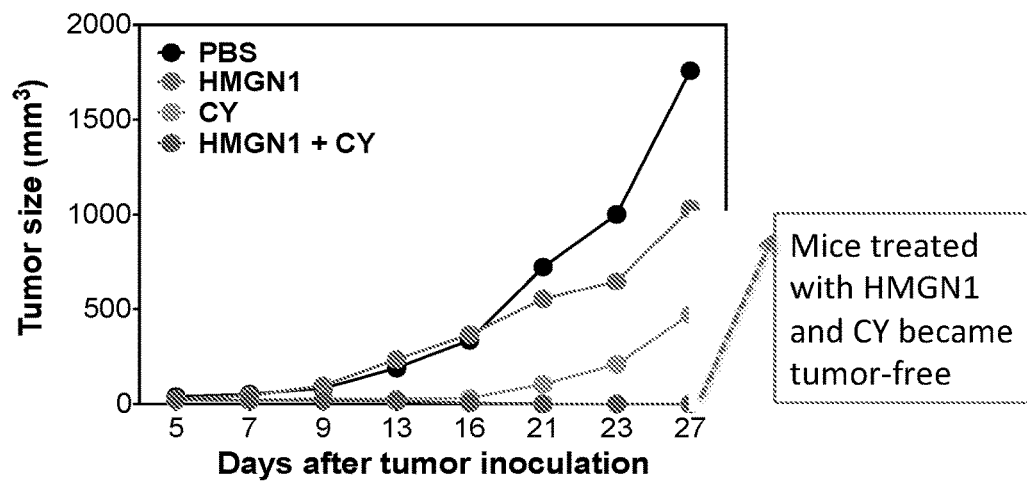

Small CT26 tumors were treated by a combination of one intraperitoneal (i.p.) injection of a suboptimal dose of cyclophosphamide or Cytoxan to reduce regulatory T cells (Treg), a key suppressor cell type in tumors, and four intratumoral (i.t.) administrations of HMGN1 within two weeks. Balb/c mice were subcutaneously inoculated with 100,000 or 200,000 CT26 cells on day 1. Tumor-bearing mice were treated as indicated in FIG. 2A. When the tumor size reached about 5 mm in diameter (by 4-6 days after tumor inoculation), mice were administered one dose of cyclophosphamide (100 mg/kg, i,p.) and/or HMGN1 protein (10 µg, intratumorally), twice a week for 2 weeks. PBS was administered i.t. or i.p. Tumor growth was monitored and plotted. As shown by FIG. 2B, treatment with HMGN1 and cyclophosphamide rendered CT26-bearing mice tumor-free.

Figure 2C:
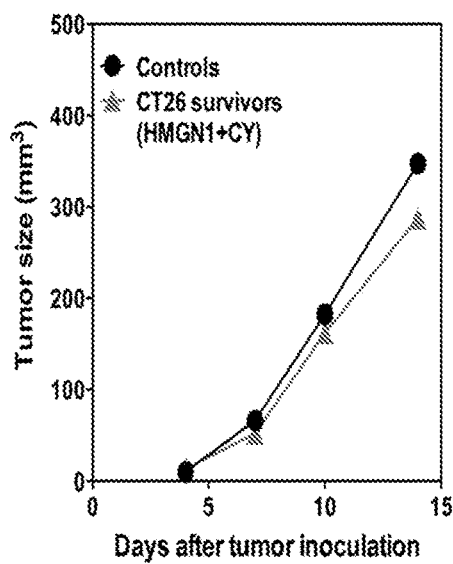
Figure 2D:
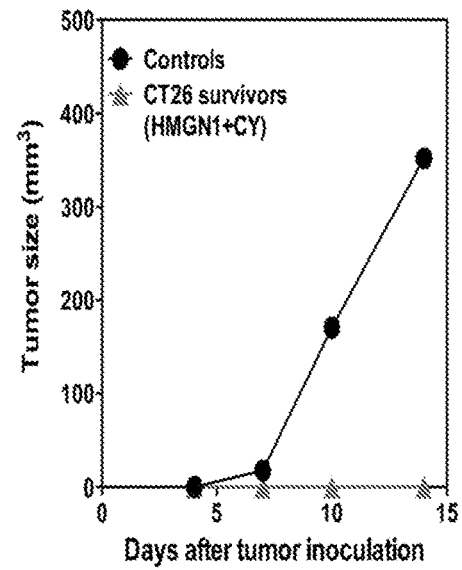

Further, HMGN1 and cyclophosphamide treated mice that recovered from CT26 tumors resisted challenge with CT26, but not 4T1 tumor cells. The protocol for rechallenge was: all mice (n=5) were inoculated subcutaneously (s.c.) with 200,000 4T1 cells to the right mammary gland and the same number of CT26 cells into the left flank. The tumor size was measured and plotted as shown in FIGS. 2C and 2D. These data demonstrate that HMGN1 and cyclophosphamide-treated mice that recovered from CT26 tumors resisted re-challenge with CT26, but not 4T1 tumor cells.

Next, big (about 1 cm diameter) established CT26 tumors were treated with a combination of HMGN1 and cyclophosphamide. However, a combination of HMGN1 and cyclophosphamide only significantly slowed down the growth of tumors, but did not eradicate the tumors. (Data not shown.)

Example 3

This example demonstrates that co-administration of HMGN1, TLR7/8 ligand resiquimod (R848), and cyclophosphamide (CYTOXAN™ or CY) successfully eradicated big (about 1 cm diameter) established CT26 tumors.

HMGN1 activates antigen-presenting dendritic cells through TLR4, while resiquimod does so via triggering TLR7/8, and therefore a combination of both was used to enhance the generation of antitumor immunity. As shown in FIG. 3, mice bearing big (1 cm diameter) CT26 tumors were treated with PBS alone, single dose of cyclophosphamide (CY), or combined single dose of CY and R848, or CY, or combined administration of R848 and HMGN1 twice a week for 2 weeks. FIG. 3A shows a schematic illustration of the administration schedule with the triple combination of CY, R848 and HMGN1 (termed TheraVac). FIG. 3B shows a tumor growth curve and representative images of tumor-bearing mice of different groups on day 21 after tumor inoculation. FIG. 3C shows the survival curve (compared with PBS group: p<0.05; p<0.01.). Data of one experiment, representative of three, are shown.

Thus, treatment with a triple combination of HMGN1, R848, and cyclophosphamide (termed TheraVac) cured mice with big established CT26 tumors.

Example 4

This example demonstrates that tumor-free mice, as a result of treatment with co-administration of HMGN1, TLR7/8 activator resiquimod (R848), and cyclophosphamide (TheraVac), generated CT26-specific immune protection.

Figure 4A:
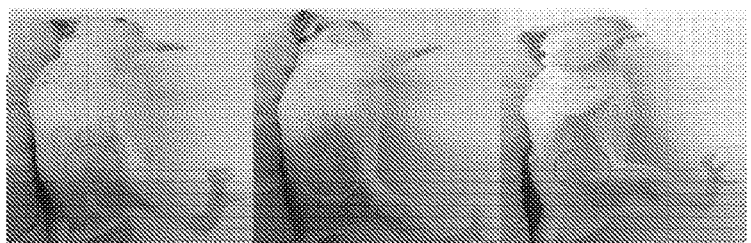
FIGS. 4A-4D show the non-appearance or appearance, respectively, of CT26 and 4T1 tumors in the flank regions of three representative mice.
Figure 4B:
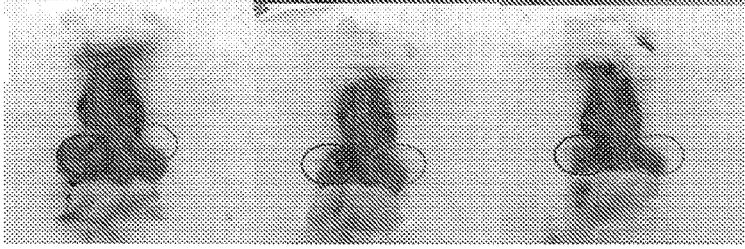
Figure 4C:
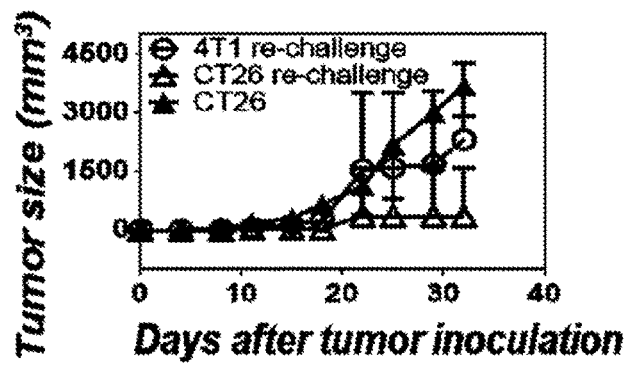
Figure 4D:
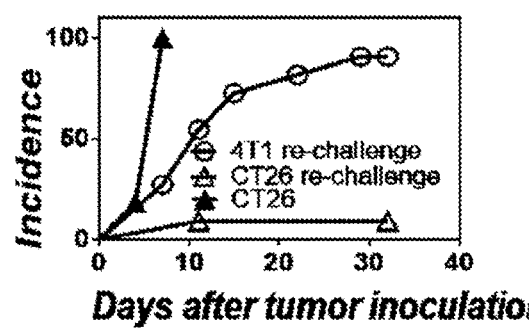

Balb/c mice with big established CT26 tumors were treated with TheraVac. The mice became tumor-free and maintained tumor-free status for 42 days. Subsequently, the tumor-free mice were re-challenged with s.c. injection of CT26 and 4T1 tumor cells in the right and left flank, respectively. The appearance of tumors in the flank regions was monitored for three weeks. The data is shown in FIG. 4. FIG. 4A shows absence of CT26 tumors in the right flank of three representative mice. FIG. 4B shows three representative mice showing the development of 4T1 tumors in the left flank but no formation of CT26 tumors in the right flank. FIGS. 4C and 4D show a summary of the results.

Thus, tumor-free mice treated by TheraVac resisted re-challenge with CT26, but did not resist re-challenge with unrelated 4T1 tumors, indicating that mice cured of CT26 tumors generated CT26-specific immune protection.

Example 5

This example demonstrates that treatment with co-administration of HMGN1, TLR7/8 activator resiquimod (R848), and cyclophosphamide (TheraVac) suppressed big established RENCA kidney tumors.

Figure 5A:
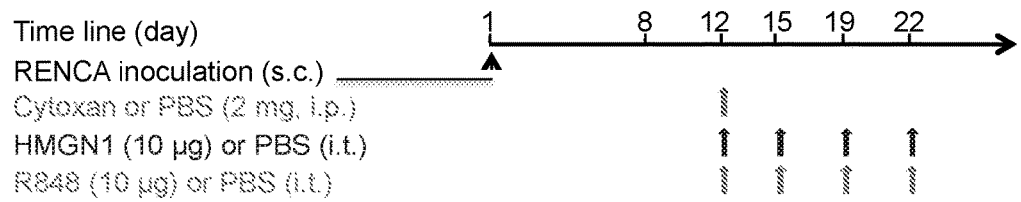
FIGS. 5A-5C show that treatment with TheraVac suppressed big established RENCA tumors.
Figure 5B:
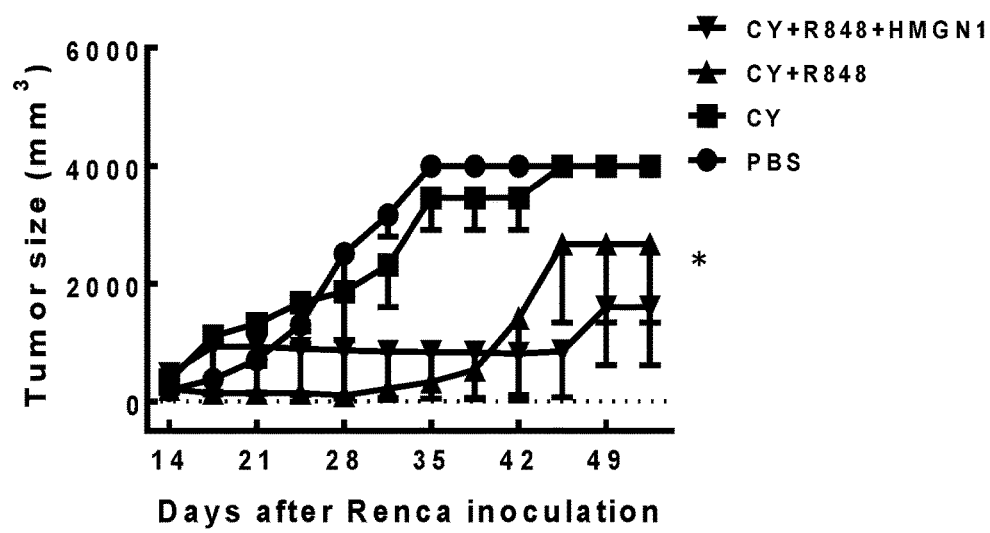
Figure 5C:
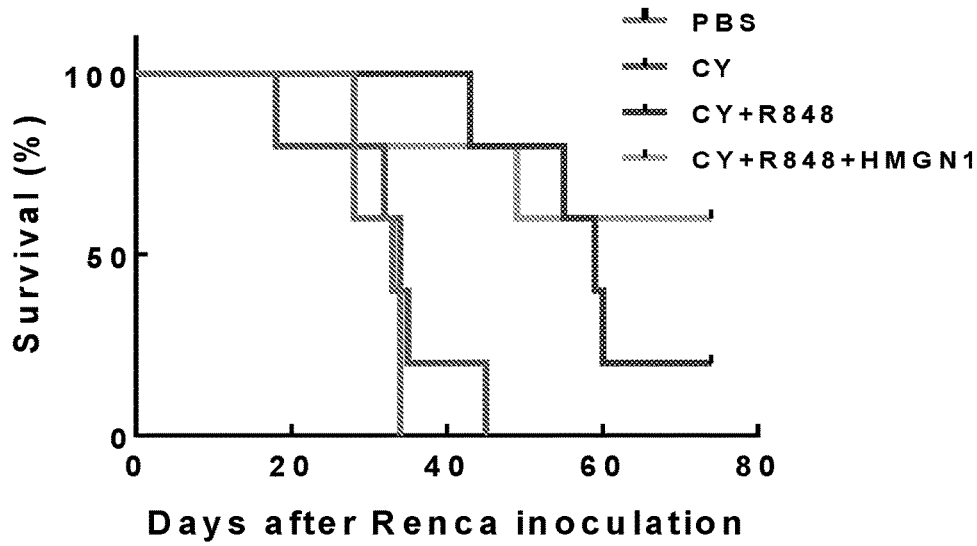

Balb/c mice were inoculated s.c. with 1,000,000 RENCA cells in PBS on day 1 and treatment started on day 12. The treatment protocol is shown in FIG. 5A. Tumor growth curve and survival curves were plotted and are shown in FIGS. 5B and 5C respectively. Data of one experiment representative of two are shown. As is evident from this figure, treatment with TheraVac successfully suppressed RENCA tumors (compared with PBS group: $*p<0.001$) and increased the survival rate.

Example 6

Figure 6A:
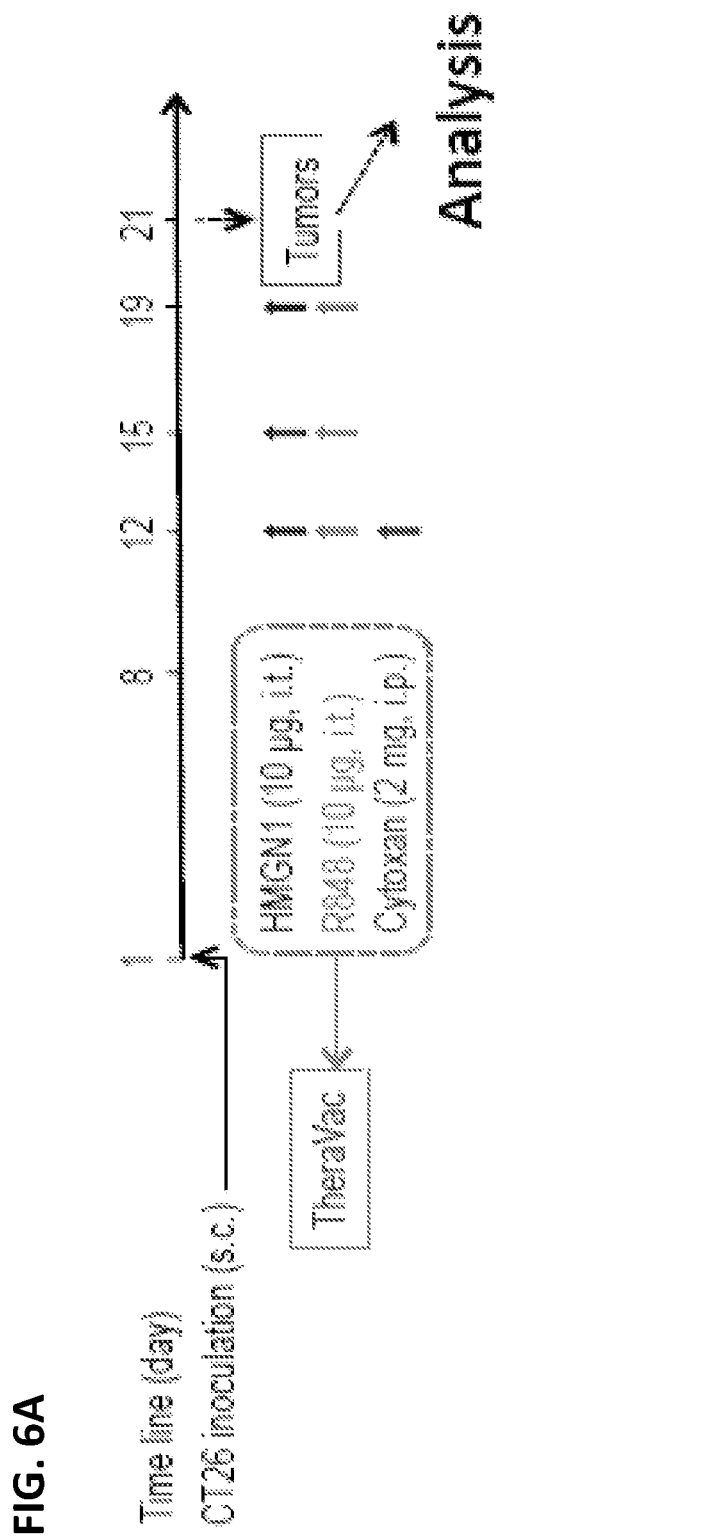
FIGS. 6A-6D show that administration of HMGN1, R848, and Cytoxan promoted the egress of dendritic cells from tumor tissue.
Figure 6B:
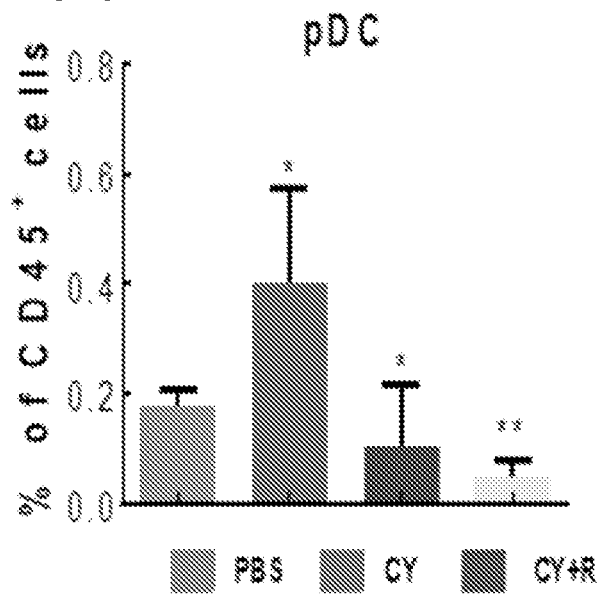
Figure 6C:
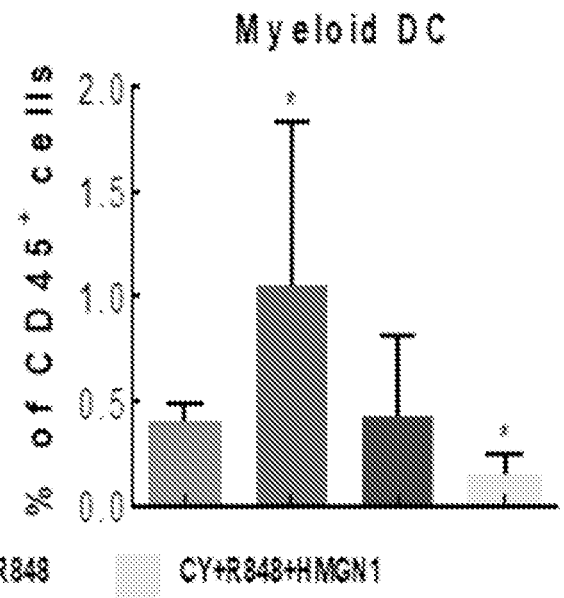
Figure 6D:
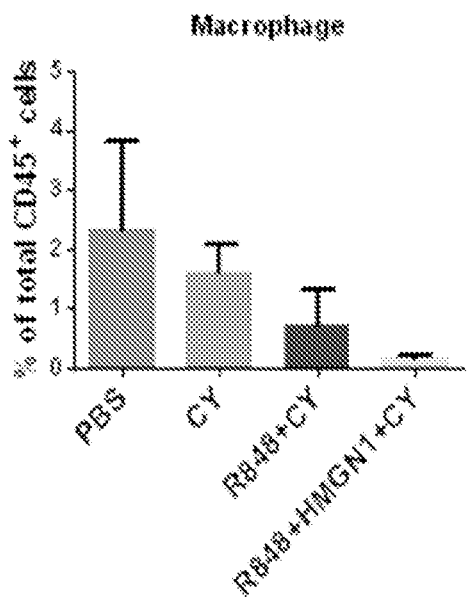

This example demonstrates that treatment with HMGN1 and R848, or HMGN1, R848 and cyclophosphamide (TheraVac) promoted the egress of dendritic cells from tumor tissue. Mice bearing big CT26 tumors were treated as indicated in FIG. 6A. Forty-eight hours after the third treatment, tumors were removed, cut into 1 mm cubes, and digested with a solution consisting of collagenase I, II, IV, deoxyribonuclease I, and elastase to make single cell suspensions. Subsequently, the single cell suspensions were stained with fluorescent dye-conjugated antibodies against CD45, CD11c, CD3, CD8, F4/80, and B220. The stained samples were analyzed by flow cytometry using LSR II. Myeloid DCs were defined as CD11c$^+$ and B220$^-$, whereas pDCs were defined as CD11c$^+$B220$^+$. Macrophages were identified as being CD45$^+$, CD11$^+$, GR1$^-$, CD3$^-$, B220$^-$ and CD11c$^-$ by FACS analysis. FIGS. 6B-6D show the average cell counts for pDC, myeloid DCs and macrophages (Mean±SEM) of three mice of each group of one experiment representative of two. Compared with PBS group, $*p<0.05$, $**p<0.01$.

Example 7

This example demonstrates that treatment with HMGN1 and R848, or HMGN1, R848 and cyclophosphamide (TheraVac) increased the number of T cells in the tumor tissue.

Figure 7A:
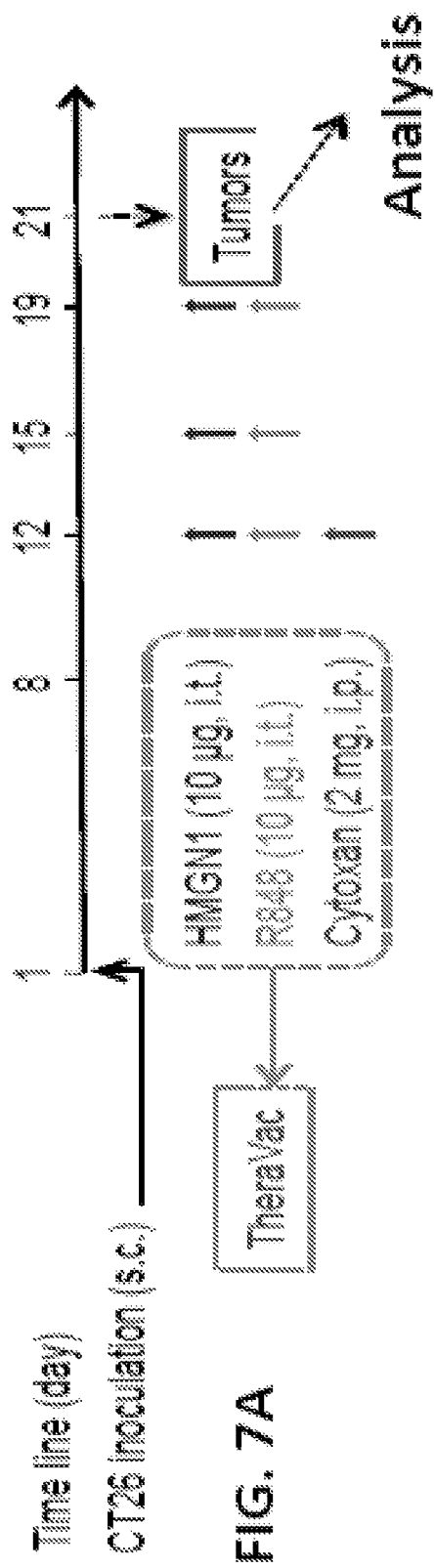

Mice bearing big CT26 tumors were treated as indicated in FIG. 7A. Forty-eight hours after the third treatment (day 21), corresponding tumors were removed, cut into 1 mm cubes, and digested with a solution consisting of collagenase I, II, IV, deoxyribonuclease I, and elastase to make single cell suspensions. The single cell suspensions of dissociated tumors were stained with fluorescent dye-conjugated antibodies against CD45, CD3, CD4, and CD8. The stained samples were analyzed by flow cytometry using LSR II. Shown in FIGS. 7B-7E are the average cell counts for CD45, CD3, CD4, and CD8 positive T cells (Mean±SEM) of three mice of each group of one experiment representative of two. Compared with PBS group, $*p<0.05$, $**p<0.01$.

Example 8

This example demonstrates that co-administration of HMGN1, TLR7/8 ligand resiquimod (R848), and anti-CTLA4 or anti-PDL1 antibodies (TheraVac) successfully eradicated various big (about 1 cm diameter) established tumors.

Figure 8A:
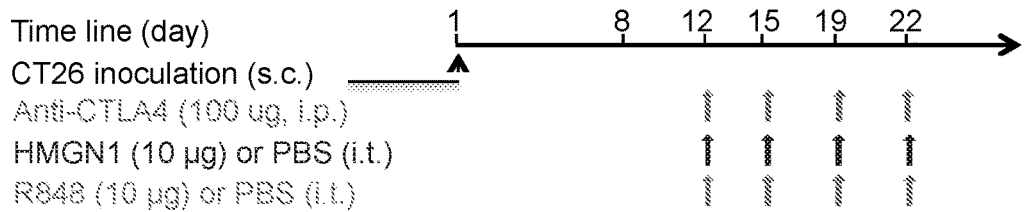
FIGS. 8A-8C show that the administration of the combination of HMGN1, R848, and an anti-CTLA4 antibody eradicated big (about 1 cm diameter), established CT26 tumors.
Figure 8B:
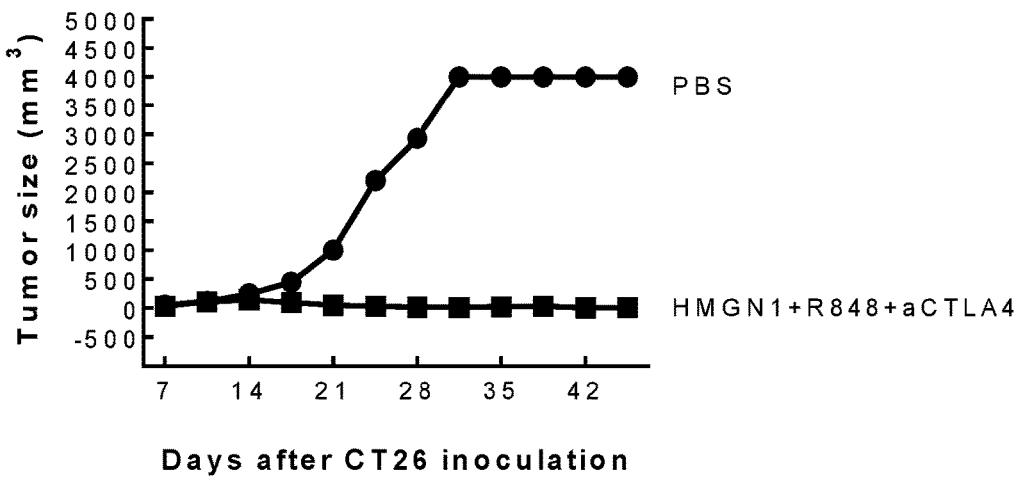
Figure 8C:
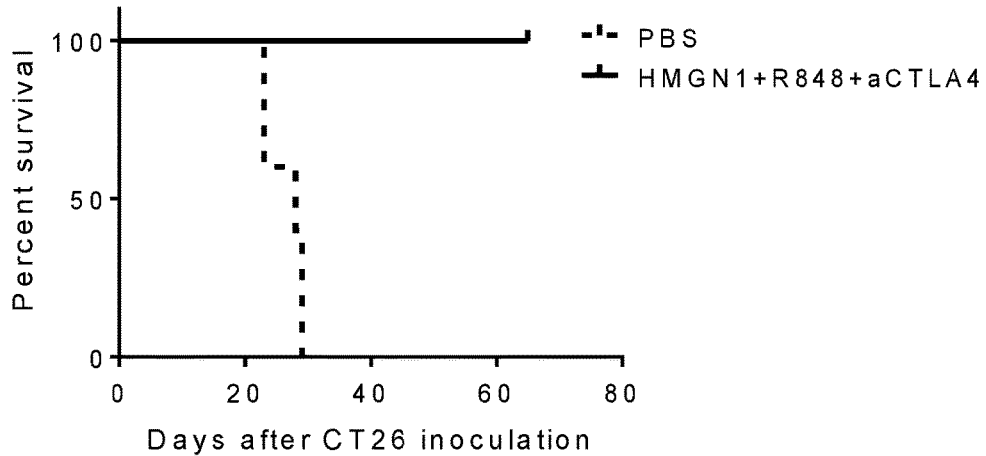

As shown in FIG. 8, mice bearing big (about 1 cm diameter) CT26 tumors were treated with PBS alone, or with HMGN1, R848 and anti-CTLA4 antibody twice a week for 2 weeks (n=5). FIG. 8A shows a schematic illustration of the experimental protocol. FIG. 8B shows tumor growth curve and FIG. 7C shows the survival curve (compared with PBS group: $**p<0.01$.) Data of one experiment, representative of three, are shown. Thus, treatment with combination of HMGN1, R848, and anti-CTLA4 antibody cured mice with big established CT26 tumors.

Figure 10:
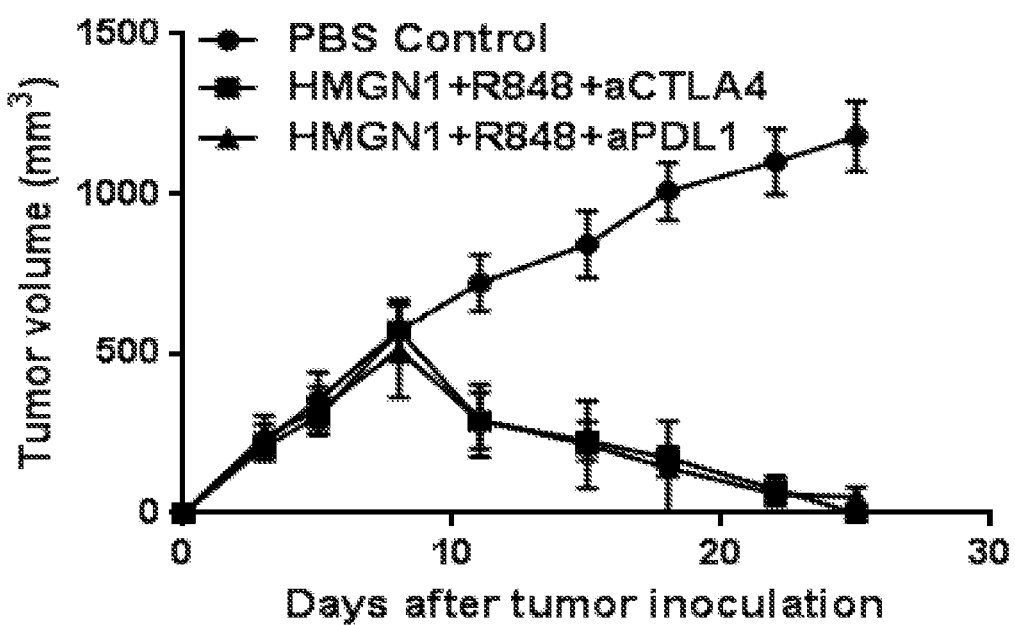
FIG. 10 shows that the administration of TheraVac suppressed big established Hepa 1-6 liver tumors.

Similar therapeutic results with Hepa 1-6 tumors were achieved with co-administration of HMGN1, R848 and anti-CTLA4 or anti-PDL1 antibodies. Mice bearing big (about 1 cm diameter) Hepa 1-6 liver tumors were treated with PBS alone, or a combination of HMGN1, R848 and anti-CTLA4 or anti-PDL1 antibody for twice a week for 2 weeks. As shown in FIG. 10, such treatment suppressed the growth of the tumors.

Example 9

This example demonstrates that co-administration of HMGN1 and TLR7/8 ligand resiquimod (R848) synergistically activates dendritic cells (DC).

Dendritic cells were incubated with HMGN1 alone (0.5 µg/ml), R848 alone (0.1 µg/ml), a combination of HMGN1 and R848, or the TLR4 ligand LPS (1 µg/ml). As shown in FIG. 9, incubation of DC with both HMGN1 and R848 resulted in activation of the cells in a synergistic manner. This is as evidenced by the synergistic increase in the production of interleukin IL12 and TNF-alpha by the DC. For instance, the production of IL-12 increased by a factor of 5-10 fold over the effect of each of these stimulants by themselves.

Example 10

This example demonstrates the development of systemic immunity upon TheraVac intratumoral injection.

Figure 11:
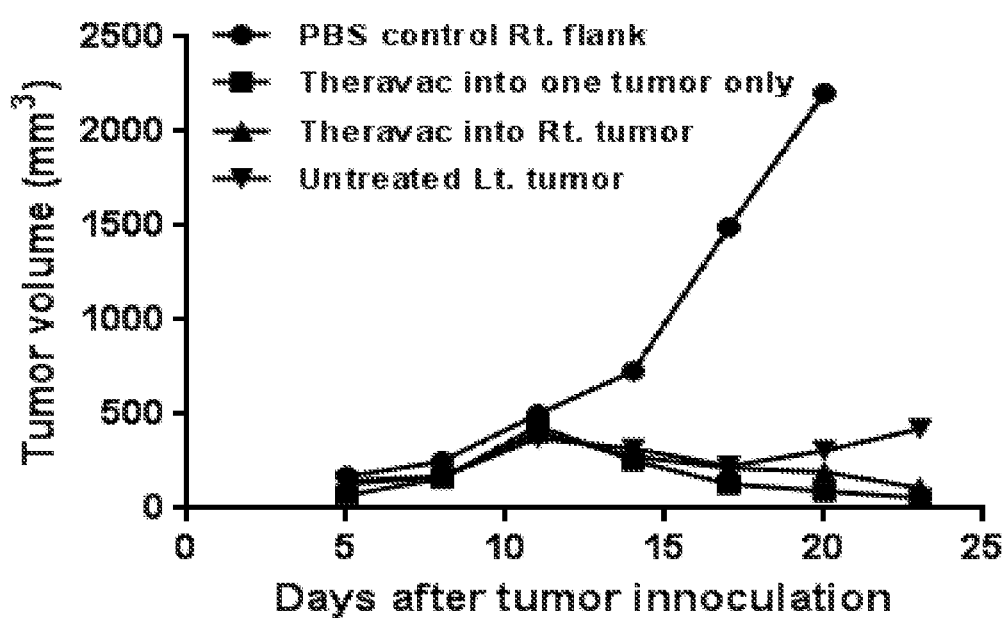
FIG. 11 shows that intratumoral TheraVac injection on the right flank suppresses the growth of CT26 tumor on the left flank.

Mice bearing CT26 tumors (approximately 1.2 cm. in diameter) were treated with PBS or a combination of intratumoral HMGN1, R848, and intraperitoneal cyclophosphamide (TheraVac) twice weekly for two weeks. Mice bearing tumors in both flanks were treated with TheraVac intratumorally only in the right flank, but received no treatment in the left flank tumor. As shown in FIG. 11, injection in only one of two tumors growing on both flanks of a mouse resulted in cure of the injected tumor and a decreased growth rate of the un-injected tumor. Thus, although intratumoral injection is more effective, systemic immunity developed and distant tumors were also partially suppressed.

Example 11

This example illustrates the preparation and characterization of Au-PEG-HMGN1-R848 nanoparticles.

Figure 12A:
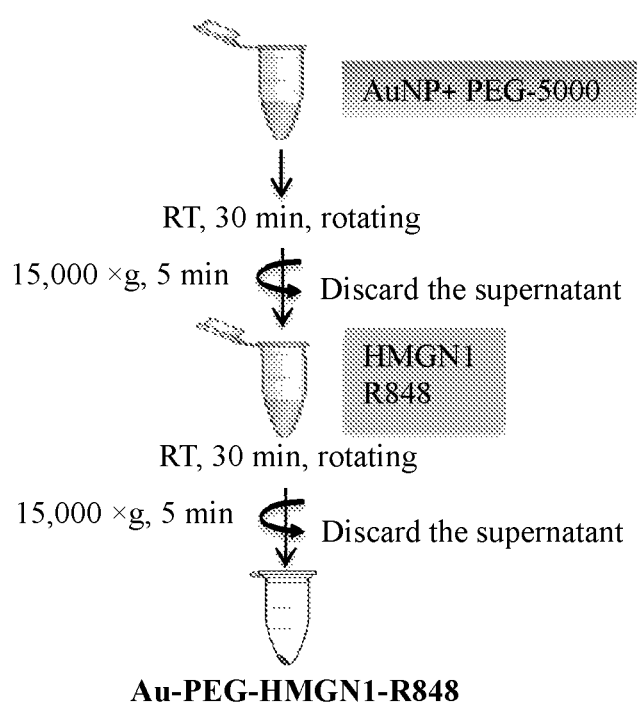
FIGS. 12A-12D depict the design and preparation of Au-PEG-HMGN1-R848 nanoparticles.

FIG. 12A presents a flowchart for the process of preparing Au-PEG-HMGN1-R848 nanoparticles. The materials used were HMGN1 at a concentration of 1 mg/ml in 10 mM Tris-HCl (pH 8), gold nanoparticles at 1 mg/ml in $H_2O$ (capping agent citrate), PEG-5000 at 3 mg/ml (added as a 20× concentrate in DI $H_2O$), and R848 at 2 mg/ml in $H_2O$. As shown in FIG. 12A, gold nanoparticles (AuNP) and PEG-5000 were mixed and rotated at room temperature for 30 minutes, and centrifuged at 15000 g for five minutes. The supernatant was discarded. Next, HMGN1 and R848 were added to the pegylated AuNP and incubated at room temperature for 30 min. The mix was rotated at room temperature for 30 minutes, and centrifuged at 15000 g for five minutes. The supernatant was discarded and the Au-PEG-HMGN1-R848 complex was recovered.

Figure 12B:
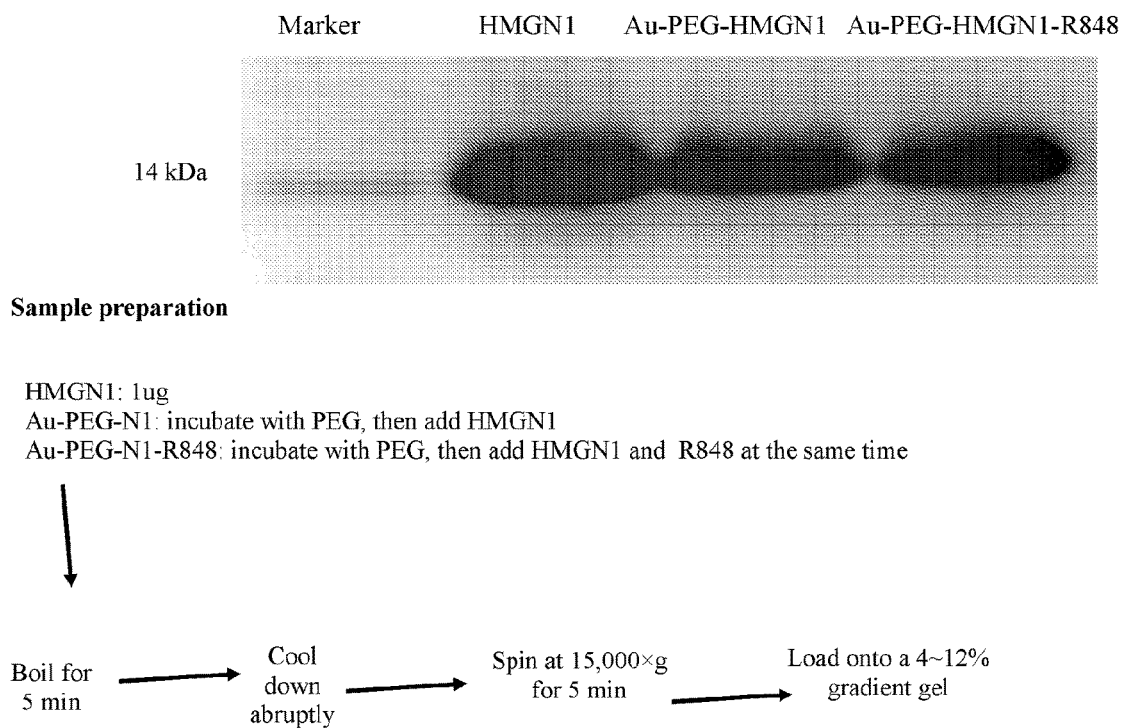
Figure 12C:
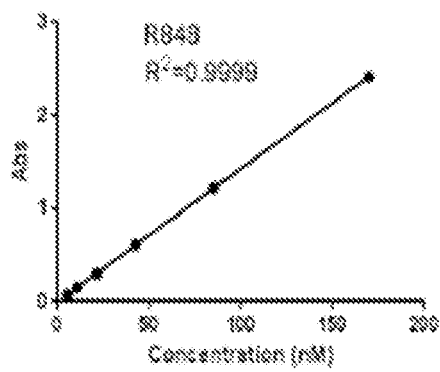
Figure 12D:
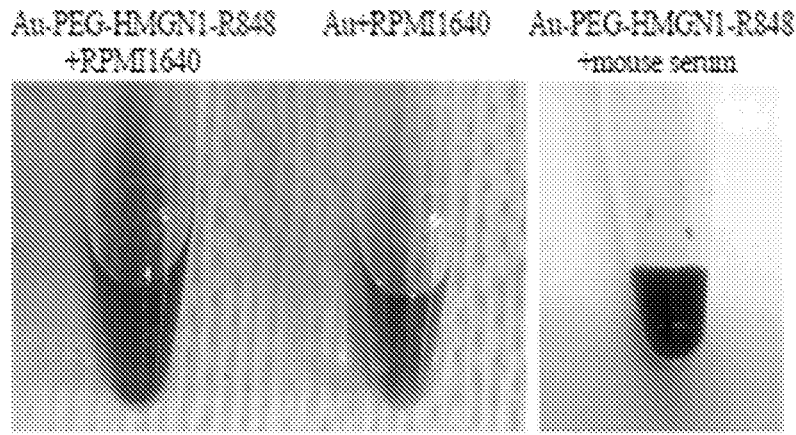

Western Blot analysis confirmed that majority of the HMGN1 was contained in the Au-PEG-HMGN1-R848 composition (see FIG. 12B). Further, absorbance of the supernatants at 320 nm (A(320)) was assayed using a NanoDrop spectrophotometer which showed that more than 60% of R848 was contained in the Au-PEG-HMGN1-R848 complex (see FIG. 12 C). The Au-PEG-HMGN1-R848 complex was stable in RPMI 1640 medium and mouse serum for over 1 month. This is shown in FIG. 12 D. No aggregation is seen in the tubes which stored Au-PEG-HMGN1-R848 nanoparticles in RPMI 1640 medium and mouse serum respectively for over a month. The color of these solutions also remained unchanged after over 1 month. In contrast, aggregates can be seen in the middle tube which contained uncoated gold particles in RPMI1640.

Figure 16:
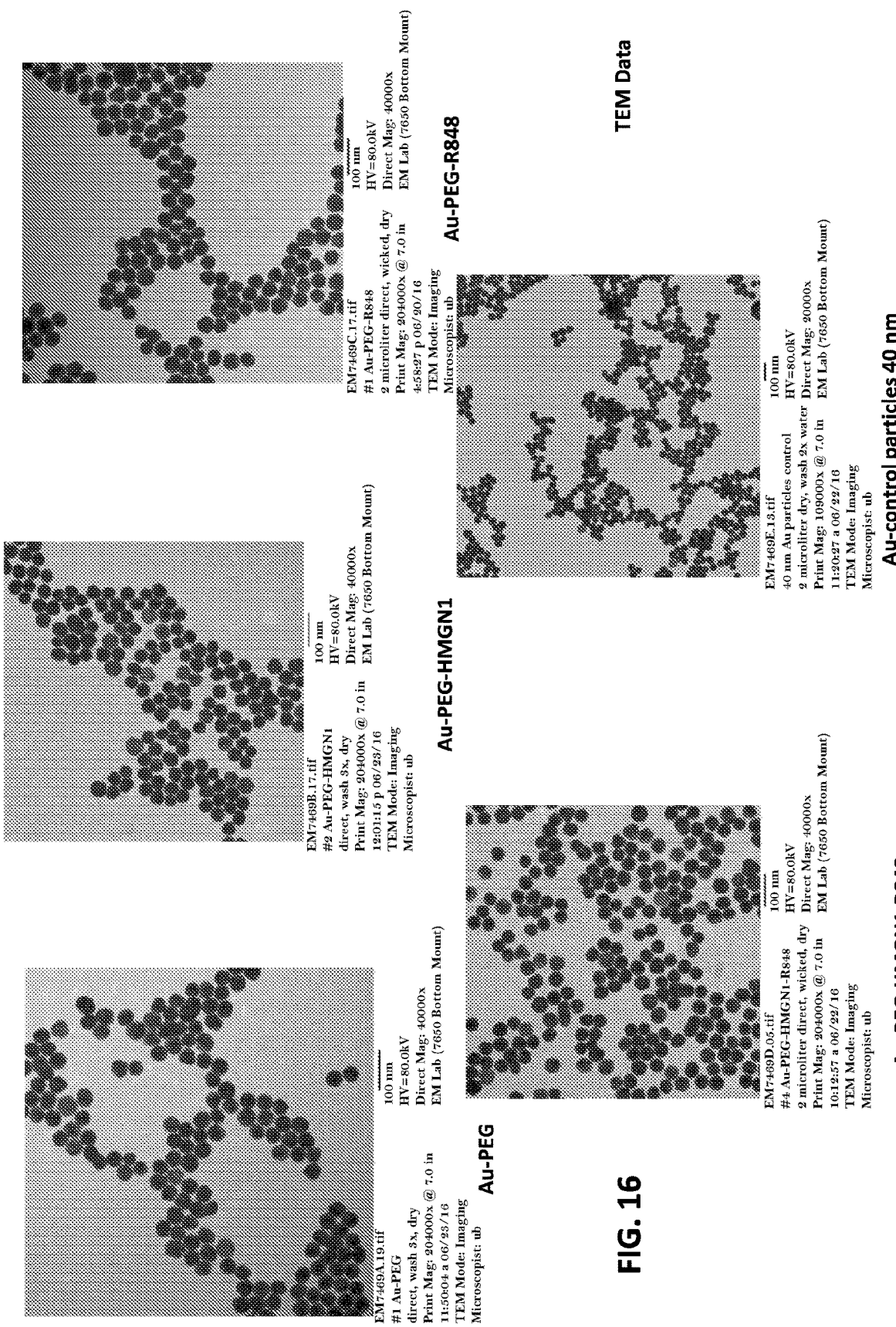
FIG. 16 shows TEM data of control gold nanoparticles, and PEGylated gold nanoparticles (Au-PEG) alone or adsorbed with HMGN-1 (Au-PEG-HMGN1), or resiquimod R848 (Au-PEG-R848), or both HMGN-1 and R848 (Au-PEG-HMGN1-R848).
Figure 19:
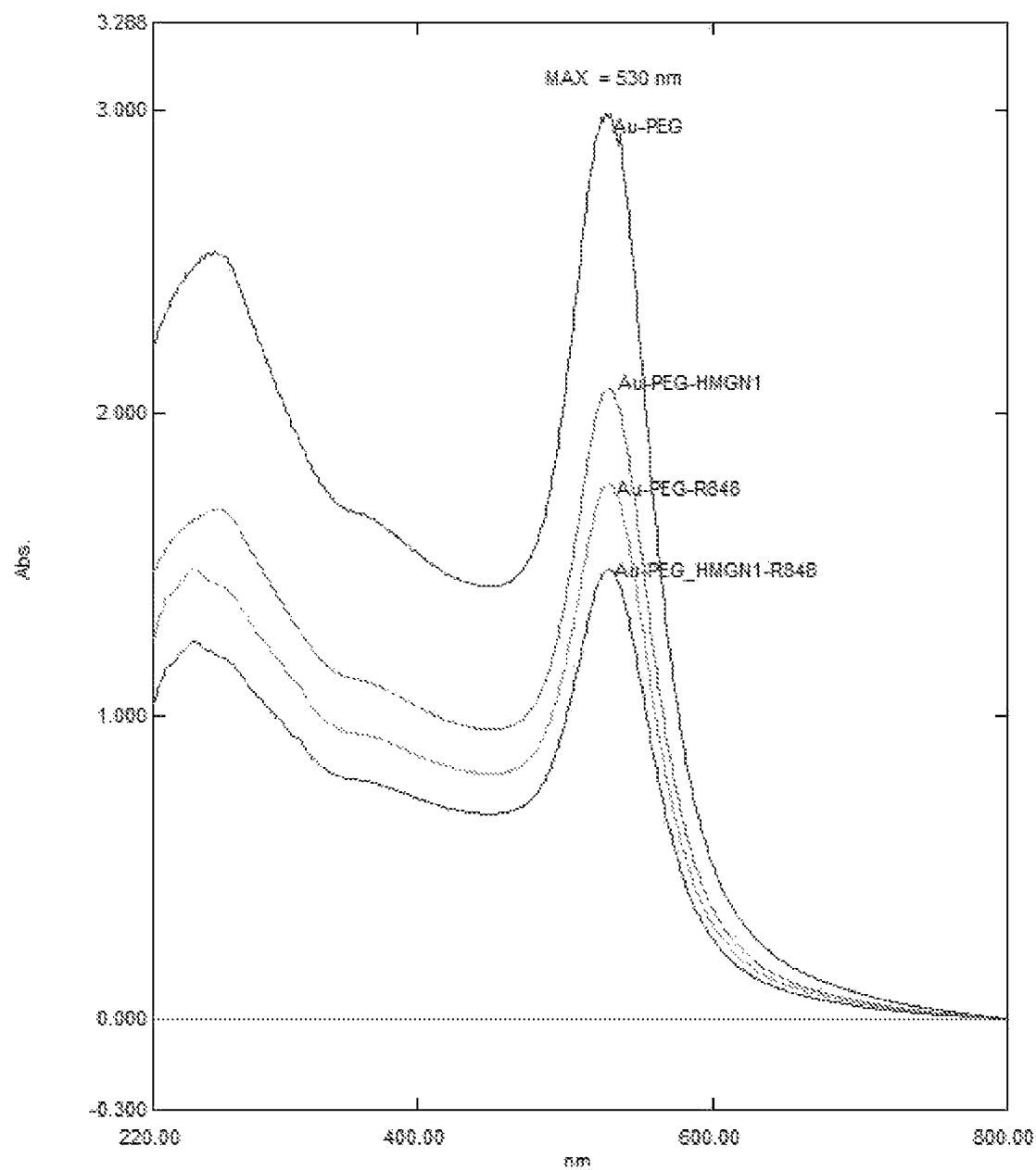
FIG. 19 shows the UV data of Au-PEG-HMGN1-R848 nanoparticles.

FIGS. 16-19 show characterization of the Au-PEG-HMGN1-R848 nanoparticles. FIG. 16 shows TEM (Transmission Electron Microscopy) data of control gold nanoparticles, and PEGylated gold nanoparticles (Au-PEG) alone or adsorbed with HMGN-1 (Au-PEG-HMGN1), or resiquimod R848 (Au-PEG-R848), or both HMGN-1 and R848 (Au-PEG-HMGN1-R848). FIGS. 17, 18, and 19 show the DLS (Dynamic Light Scattering) data, zeta potential data, and UV data of Au-PEG-HMGN1-R848 nanoparticles respectively. The average diameter of the citrate-stabilized gold nanoparticles was about 40 nm and the average hydrodynamic diameter of the Au-PEG-HMGN1-R848 nanoparticles was about 50 nm.

Example 12

This example illustrates that Au-PEG-HMGN1-R848 nanoparticles is capable of inducing DC maturation.

Figure 13:
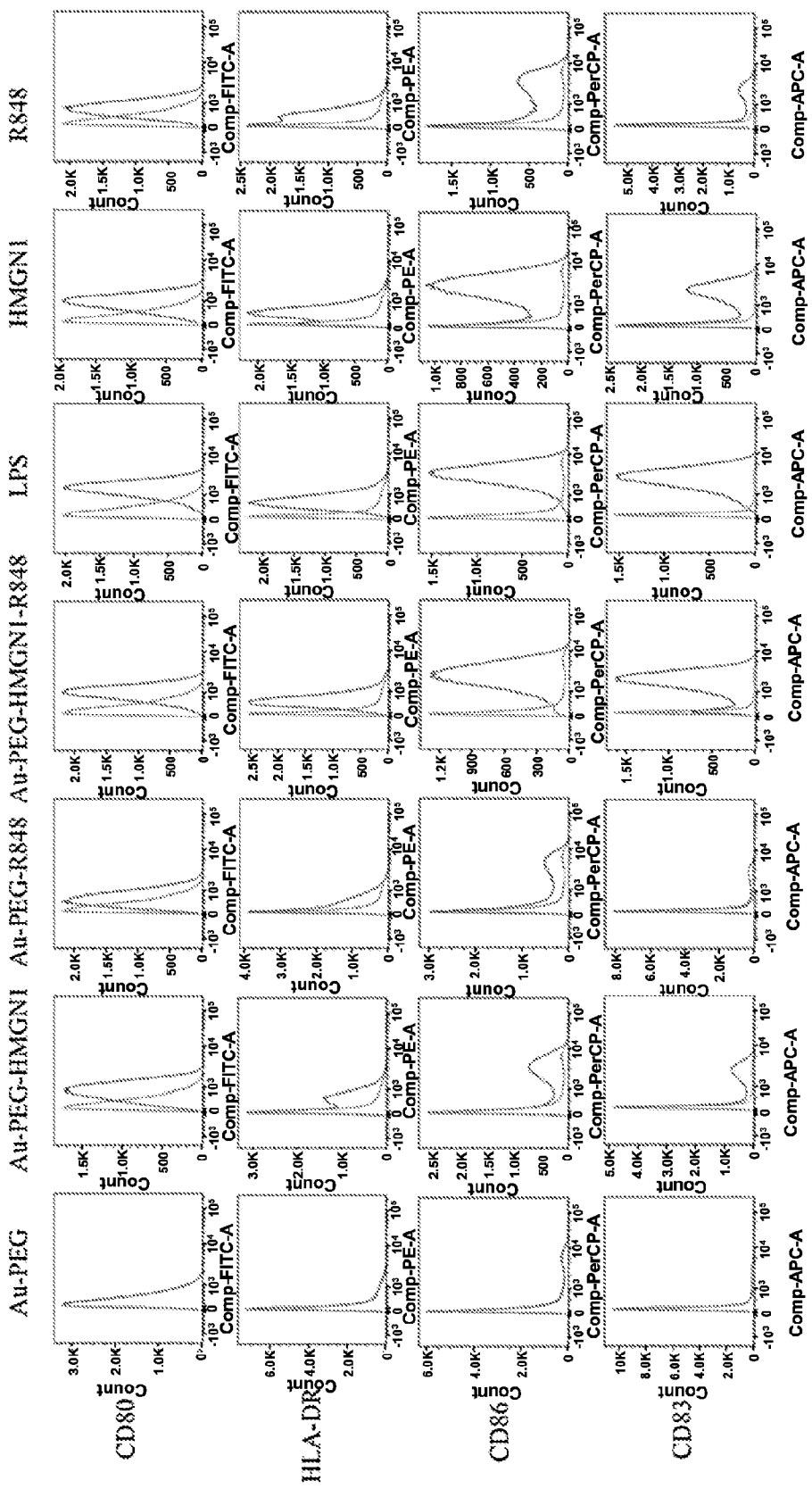
FIG. 13 shows flow cytometry data indicating that Au-PEG-HMGN1-R848 nanoparticles are capable of inducing DC maturation.

Human DCs were incubated with Au-PEG, Au-PEG-HMGN1, Au-PEG-R848, Au-PEG-HMGN1-R848, LPS, HMGN1 and R848 for 24 hr, followed by immunostaining and assayed by Flow cytometry. Au-PEG-HMGN1-R848 stimulated the maturation of human DCs by upregulating CD83, CD86, HLA-DR, and CD80 (FIG. 13). Overlay histogram with the expression of surface molecules by sham-treated (PBS-treated) DCs shown in Blue (left peak).

Example 13

This example illustrates that Au-PEG-HMGN1-R848 accumulates in the tumors in vivo.

Figure 14:
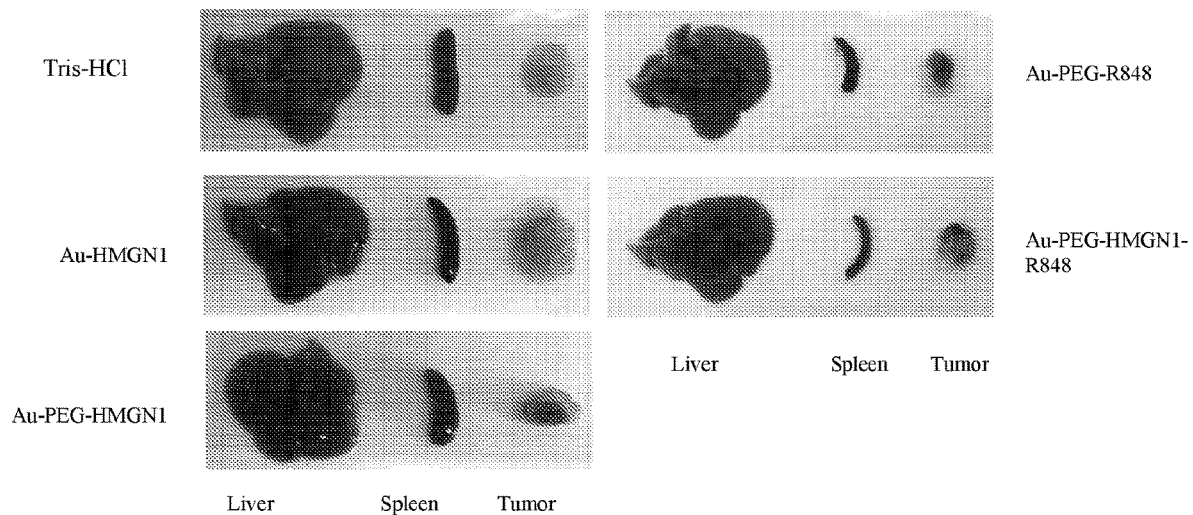
FIG. 14 shows that Au-PEG-HMGN1-R848 nanoparticles accumulate in the tumors in vivo.

Hepa 1-6 tumor-bearing mice were intravenously injected with 0.1 ml Tris-HCl, Au-HMGN1, Au-PEG-HMGN1, Au-PEG-R848 or Au-PEG-HMGN1-R848. Five hours after injection, mice were euthanized to remove spleen, liver, and tumor and the color of the organ was determined. The accumulation of Au-PEG-HMGN1-R848 was evidenced by a marked change in the color of the organs or tumor (FIG. 14).

Example 14

This example illustrates the therapeutic effect of the intravenously administered Au-PEG-HMGN1-R848 nanoparticles and cyclophosphamide.

Figure 15:
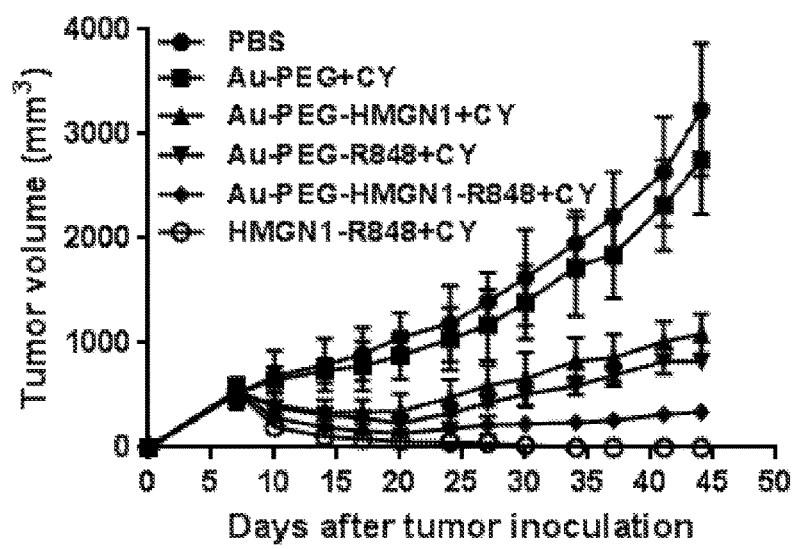
FIG. 15 shows the therapeutic effect of the intravenously-administered Au-PEG-HMGN1-R848 nanoparticles and cyclophosphamide (Cytoxan).

Mice were injected s.c. with 0.2 ml of Hepa 1-6 suspension ($10^7$/ml in PBS) into the right flanks on day 1. When tumors reached approximately 1.0 mm in diameter (usually around Day 7-8), tumor-bearing mice were treated with cyclophosphamide along with intratumoral administration of HMGN1 and R848, or intravenous administration of Au-PEG-HMGN1, Au-PEG-R848 or Au-PEG-HMGN1-R848 complex twice weekly for two weeks. Administration of intravenous cyclophosphamide with intratumor injection cured 5/5 mice, while intravenous treatment with cyclophosphamide and the Au-PEG-HMGN1-R848 on nanoparticles cured 3/5 mice (FIG. 15).

The present invention has been described in detail, including the preferred embodiments thereof. However, it will be appreciated that those skilled in the art, upon consideration of the present disclosure, may make modifications and/or improvements of this invention and still be within the scope and spirit of this invention as set forth in the following claims. All publications and patent documents cited in this application are incorporated by reference in their entirety for all purposes to the same extent as if each individual publication or patent document were so individually denoted.

The invention claimed is:

1. A method of treating cancer or reducing the incidence of relapse of a cancer in a subject comprising:
    co-administering a) a Toll-like receptor (TLR) 4 ligand, b) a TLR7 or 8 ligand, and c) a checkpoint inhibitor to the subject, thereby treating the cancer or reducing the incidence of relapse of the cancer, wherein the TLR4 ligand is HMGN1 protein.

2. The method of claim 1, wherein the HMGN1 protein, TLR7 or TLR8 ligand and immune checkpoint inhibitor are administered in the absence of a tumor antigen.

3. The method of claim 1, wherein the TLR7 or TLR8 ligand is resiquimod, imiquimod, an imidazoquinoline derivative, 852A, VTX1463, AZD8848, ANA773, or a combination thereof.

4. The method of claim 1, wherein the immune checkpoint inhibitor is
    i) cyclophosphamide,
    ii) an anti-CTLA4, anti-PD1, anti-PDL1, anti-PDL2, anti-LAG-3, anti-BTLA, anti-B7H3, anti-B7H4, anti-TIM3, or an anti-A2aR antibody, or
    iii) combinations of i) and ii).

5. The method of claim 1, comprising co-administration of the HMGN1 protein, resiquimod and cyclophosphamide.

6. The method of claim 5, wherein the cyclophosphamide is administered to the patient at a dose of about 100 mg/kg or less.

7. The method of claim 1, comprising co-administration of the HMGN1 protein, resiquimod and an anti-CTLA antibody.

8. The method of claim 1, wherein the cancer is a solid tumor, a thymoma, colon cancer, kidney cancer, or liver cancer.

9. The method of claim 1, wherein the co-administration comprises intratumoral, intraperitoneal, intravenous, or intramuscular injection of at least the HMGN1 protein.

10. The method of claim 1, wherein HMGN1 protein is administered by intratumoral injection.

11. The method of claim 1, wherein the HMGN1 protein and the TLR7 or TLR8 ligand is administered sequentially or simultaneously.

12. The method of claim 1, wherein the HMGN1 protein and the TLR7 or TLR8 ligand are administered in the absence of a tumor antigen.

13. The method of claim 1, comprising administering a composition comprising a nanoparticle adsorbed with the HMGN1 protein and the TLR 7 or 8 ligand.

14. The method of claim 13 wherein the nanoparticle is a gold nanoparticle.

15. The method of claim 14, wherein the nanoparticle is PEGylated.

16. The method of claim 15, wherein the nanoparticle has an average diameter of between about 10 nm and about 100 nm.

17. The method of claim 15, wherein the nanoparticle has an average zeta potential between about −40 mV and about +40 mV.

18. The method of claim 14, wherein the composition comprises between about 70% and about 96% gold.

19. The method of claim 15, wherein the composition comprises between about 2% and about 22% polyethylene glycol (PEG).

20. The method of claim 13, wherein the composition comprises between about 0.5% and about 10% HMGN1.

21. The method of claim 13, wherein the composition comprises between about 0.5% and about 10% TLR 7 or 8 ligand.

22. The method of claim 13, wherein the TLR7 or TLR8 ligand is resiquimod, imiquimod, an imidazoquinoline derivative, 852A, VTX1463, AZD8848, or a combination thereof.

23. A composition comprising an HMGN1 protein, a Toll-like receptor (TLR) 7 or 8 ligand adsorbed to a nanoparticle, and an immune checkpoint inhibitor, and wherein the immune checkpoint inhibitor comprises:
   i) cyclophosphamide,
   ii) an antibody, wherein that antibody is an anti-CTLA4, anti-PD1, anti-PDL1, anti-PDL2, anti-LAG-3, anti-BTLA, anti-B7H3, anti-B7H4, anti-TIM3, or an anti-A2aR antibody, and
   iii) combinations of i) and ii).

24. The composition of claim 23, wherein the nanoparticle is a gold nanoparticle.

* * * * *